US008236984B2

(12) United States Patent
Pepys et al.

(10) Patent No.: US 8,236,984 B2
(45) Date of Patent: Aug. 7, 2012

(54) COMPOUND AND USE THEREOF IN THE TREATMENT OF AMYLOIDOSIS

(75) Inventors: Mark Brian Pepys, London (GB); Steven Victor Ley, Cambridge (GB); Angus John Morrison, Glasgow (GB); Vittorio Bellotti, Pavia (IT); Simon Kolstoe, Botley (GB); Martin Smith, Oxford (GB)

(73) Assignee: Pentraxin Therapeutics Ltd., London (GB)

( * ) Notice: Subject to any disclaimer, the term of this patent is extended or adjusted under 35 U.S.C. 154(b) by 211 days.

(21) Appl. No.: 12/728,361

(22) Filed: Mar. 22, 2010

(65) Prior Publication Data
US 2010/0249233 A1 Sep. 30, 2010

Related U.S. Application Data

(63) Continuation-in-part of application No. PCT/EP2008/062879, filed on Sep. 25, 2008.

(30) Foreign Application Priority Data

Sep. 25, 2007 (GB) ................................ 0718718.0

(51) Int. Cl.
C07C 63/33 (2006.01)
A01N 37/30 (2006.01)
(52) U.S. Cl. ....................................... 562/491; 514/555
(58) Field of Classification Search .......................... None
See application file for complete search history.

(56) References Cited

FOREIGN PATENT DOCUMENTS
WO WO 02/05813 1/2002
WO WO 03/013508 2/2003

OTHER PUBLICATIONS

Database CAPLUS Chemical Abstracts Service, Columbus, Ohio, US; Database Accession No. 1955:16199, Abstract of GB 699141.*
Database CAPLUS Chemical Abstracts Service, Columbus, Ohio, US; Database Accession No. 1961:98259, Abstract of Frumina et al., Zhurnal Analiticheskoi Khimii (1960), 15, 671-5.*
Database CAPLUS Chemical Abstracts Service, Columbus, Ohio, US; Database Accession No. 1913:9250, Abstract of Cain et al., Proceedings of the Chemical Society, London (1913), 28, 285.*
Nora S. Green, et al., Synthesis and Characterization of Potent Bivalent Amyloidosis Inhibitors That Bind Prior to Transthyretin Tetramerization , J. Am. Chem. Soc. (2003) vol. 125, p. 13404-13414. Steven M. Johnson, et al., Native State Kinetic Stabilization as a Strategy to Ameliorate Protein Misfolding Diseases: A Focus on the Transthyretin Amyloidoses, Acc. Chem. Res. (2005) vol. 38, No. 12, p. 911-921.
M. B. Pepys, Pathogenesis, Diagnosis and Treatment of Systemic Amyloidosis, Phil. Trans. R. Soc. Lond. B (2001) vol. 356, p. 203-211.
Hans E. Purkey, et al., Evaluating the Binding Selectivity of Transthyretin Amyloid Fibril Inhibitors in Blood Plasma, PNAS (2001) vol. 98, No. 10, p. 5566-5571.

* cited by examiner

*Primary Examiner* — Karl J Puttlitz
(74) *Attorney, Agent, or Firm* — Vedder Price P.C.; Thomas J. Kowalski; Raymond Chung

(57) ABSTRACT

The present invention relates to compounds of formula (I) for stabilizing the tetrameric form of transthyretin, compounds for use in the treatment or prevention of amyloidosis, and agents and medicaments comprising such compounds.

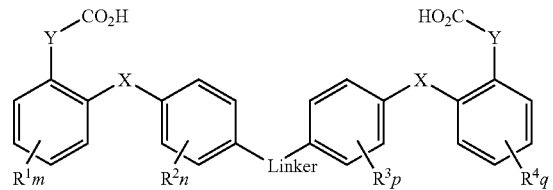

wherein X, Y, $R^1$, $R^2$, $R^3$, $R^4$, m, n, p, q, and the linker are as defined herein.

18 Claims, 21 Drawing Sheets

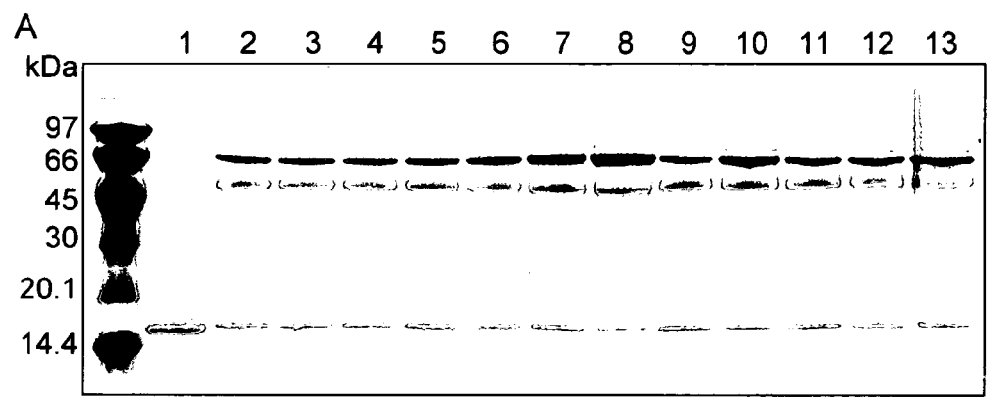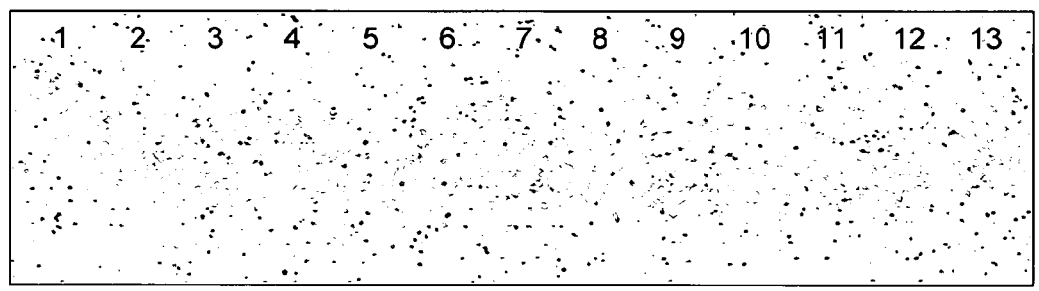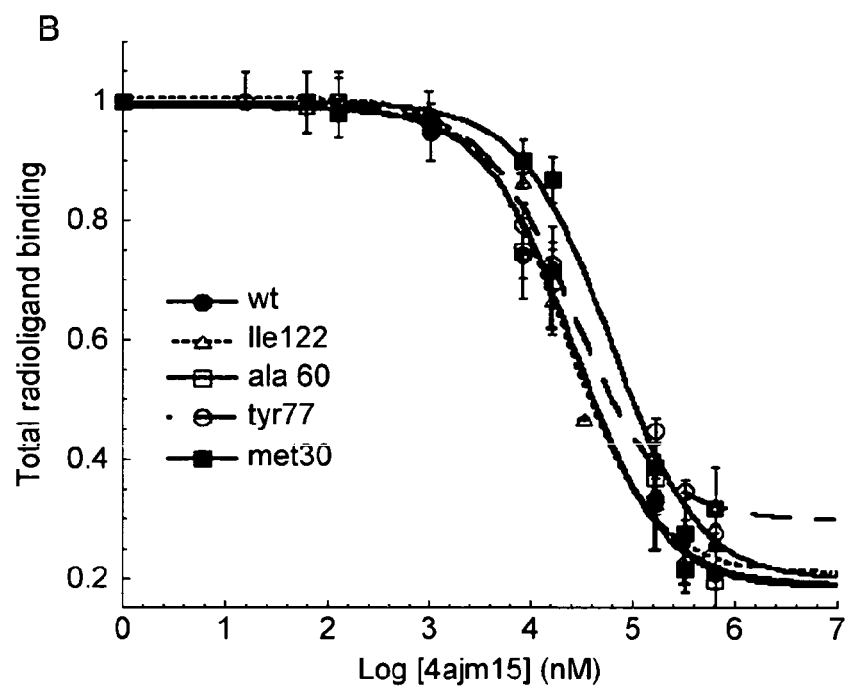
FIG. 3

COMPOUND AND USE THEREOF IN THE TREATMENT OF AMYLOIDOSIS

This application is a continuation-in-part application of international patent application Serial No. PCT/EP2008/062879 filed 25 Sep. 2008, which published as PCT Publication No. WO 2009/040405 on 2 Apr. 2009, which claims priority to GB application Serial No. 0718718.0 filed 25 Sep. 2007.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

It is noted that in this disclosure, terms such as "comprises", "comprised", "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, nonobvious, inventive, over the prior art, e.g., over documents cited herein or incorporated by reference herein. And, the terms "consists of" and "consisting of" have the meaning ascribed to them in U.S. patent law; namely, that these terms are closed ended.

The embodiments of the present invention are disclosed herein or are obvious from and encompassed by, the detailed description. The detailed description is given by way of example but not intended to limit the invention solely to the specific embodiments described.

The present invention relates to compounds for stabilising the tetrameric form of transthyretin, compounds for use in the treatment or prevention of amyloidosis, and agents and medicaments comprising such compounds.

INCORPORATION BY REFERENCE

This application claims priority to UK Provisional Patent Application No. 0718718.0 filed Sep. 25, 2007.

The above referenced application, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them; e.g., they can mean "includes", "included", "including" and the like. Terms such as "consisting essentially of" and "consists essentially of" have the meaning attributed to them, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, nonobvious, inventive, over the prior art, e.g., over documents cited herein or incorporated by reference herein. And, the terms "consists of" and "consisting of" have the meaning ascribed to them; namely, that these terms are closed ended.

These and other embodiments are disclosed or are obvious from and encompassed by, the following Detailed Description.

BACKGROUND TO THE INVENTION

Amyloidosis is a serious disease caused by extracellular deposition of insoluble abnormal fibrils (Pepys, 2006). Systemic amyloidosis, with deposits in the viscera, blood vessels and connective tissue, is usually fatal, causing about one per thousand deaths in developed countries. About 25 different unrelated human proteins form amyloid fibrils in vivo. Amyloid is deposited when there is: (i) sustained exposure to either normal or increased concentrations of a normal, potentially amyloidogenic, protein; (ii) when an abnormal amyloidogenic protein is produced as a consequence of an acquired disease; or (iii) when a gene mutation encodes an amyloidogenic variant protein. Fibrillogenesis results from reduced stability of the native fold of the fibril precursor protein, so that under physiological conditions it populates partly unfolded intermediate states which aggregate as stable amyloid fibrils with the pathognomonic cross-β sheet core structure (Sunde et al 1997).

Wild type transthyretin, the normal plasma protein which transports thyroid hormone and retinol binding protein, is inherently amyloidogenic and forms microscopic amyloid deposits of uncertain clinical significance in all individuals aged over 80 years. Massive deposits in the heart can also occur, causing fatal senile cardiac transthyretin amyloidosis. The inherent amyloidogenicity of wild type transthyretin is markedly enhanced by most of the reported >80 different point mutations which encode single residue substitutions in the transthyretin sequence (Saraiva, 2002). These mutations cause autosomal dominant adult onset hereditary amyloidosis, a universally fatal condition affecting about 10,000 patients worldwide. The usual clinical presentation is familial amyloid polyneuropathy, with predominant peripheral and autonomic neuropathy, but there is commonly also serious involvement of the heart, kidneys and eyes. The condition typically presents after the causative gene has been transmitted to the proband's offspring, ensuring persistence of this devastating disease. Amyloidogenic mutations occur in all ethnic groups, but by far the most common, V30M, clusters in three geographical foci: Northern Portugal, Northern Sweden and parts of Japan. A common amyloidogenic variant in the UK and Eire is T60A. Transthyretin amyloidosis predominantly affecting the heart is particularly associated with the V122I variant, which is very rare in Caucasians but is carried by 4% of African Americans: 1.3 million people, including 13,000 individuals homozygous for the mutation (Jacobson, 1997). It is the second most common pathogenic mutation in that population after sickle cell haemoglobin. Cardiac transthyretin amyloidosis presents as progressive, ultimately fatal, heart failure due to restrictive cardiomyopathy, is rarely suspected and is usually misdiagnosed as coronary heart disease.

Liver transplantation provides an effective treatment for some patients with transthyretin amyloidosis. Transthyretin is synthesized by hepatocytes and by the choroid plexus. Liver transplantation removes the source of the amyloidogenic variant transthyretin in the plasma and replaces it with wild type transthyretin, however the procedure is available for only a minority of patients. There is a severe shortage of donor livers and the diagnosis of transthyretin amyloidosis is often too late for optimal results to be obtained. Patients with mutations other than V30M can develop rapidly progressive cardiac amyloidosis after transplantation. In patients with predominant cardiac amyloid, heart transplantation is a possible option, but most are too old and are not acceptable recipients for scarce donor organs. Furthermore liver transplantation does not affect production of variant amyloidogenic transthyretin by the choroid plexus and deposition of transthyretin amyloid in the eye and leptomeninges can thus progress despite disappearance of variant transthyretin from the circulation.

In view of the limitations of transplantation therapy, therapeutic drug approaches have been investigated. The native transthyretin molecule is very well characterised and is a homotetramer of molecular weight 55,044 Da, and the non-covalently associated protomers, of mass 13,761, each contain 127 residues with a β-sandwich fold. The native tetramer binds a single retinol binding protein molecule and contains two identical negatively cooperative L-thyroxine (T4) binding pockets. Amyloid fibril formation by transthyretin involves dissociation of the tetramer, partial unfolding of the protomers and then aggregation into the amyloid cross-β core structure.

One therapeutic drug approach is taught in WO03/013508 which describes agents comprising ligands capable of being bound by transthyretin which are covalently co-linked by a linker. The purpose of these agents is to form complexes between separate transthyretin tetramers in the subject to be treated. This approach relies on the complexes being recognised by the body as abnormal and rapidly cleared from the circulation. In this way, the amyloidogenic protein is no longer available as a source for amyloid deposition.

Another approach to the potential treatment of transthyretin amyloidosis has been to identify small molecule ligands which are specifically bound in the thyroid hormone binding pocket so as to stabilise the native transthyretin tetrameric structure and thereby prevent dissociation into dimers and protomers leading to fibrillogenic aggregation. This approach is described, for example, in WO2004/05635 where an array of biphenyl and benzoxazole compounds are described, including 2-(3,5-dichlorophenyl)benzo[d]oxazole-6-carboxylic acid (6). In the academic literature, in vitro studies have shown that bis-arylamine compounds have affinity for the binding pocket in transthyretin and can stabilise the tetrameric form. Oza et al (2002) describe the structures of various compounds of this type. In this paper, a distinction is made between a "forward mode" of binding and a "reverse mode". Oza et al is particularly concerned with analogues of diclofenac (1), which has a ring bearing a chlorine substituent and a second ring bearing a carboxylate group. The diclofenac analogue, 2-(3,5-dichlorophenyl amino)benzoic acid (2) and diclofenac itself both bind in the "reverse mode" with the carboxylate bearing ring occupying the inner binding cavity of the transthyretin binding pockets. Wiseman et al (2005) also shows compound (2) binding in reverse mode.

Green et al (2003) describe various bivalent inhibitors of transthyretin which comprise a pair of ligands linked together by a linker. When bound by the transthyretin tetramer, each ligand is situated in a binding pocket and the linker is situated in a central channel that runs through the transthyretin tetramer. The linker was therefore covalently attached to the aromatic group intended for binding to the inner binding cavity of the binding pockets. Whilst the authors found that these bivalent inhibitors stabilised tetrameric transthyretin reconstituted from dissociated protomers, these inhibitors were generally poor in the standard transthyretin fibril formation assay indicating that they were not bound at all by native tetrameric transthyretin. These results suggest that the approach of transthyretin stabilisation by bivalent compounds would not be successful in the treatment or prevention of transthyretin amyloidosis.

SUMMARY OF THE INVENTION

The present invention aims to provide agents or compounds with improved properties over those described in the prior art and which are suitable for use particularly in the treatment or prevention of transthyretin amyloidosis.

Accordingly, in a first aspect, there is provided an agent for stabilising the tetrameric form of transthyretin, which comprises a compound of the general formula (I) or a pharmaceutically acceptable salt, ester or prodrug thereof:

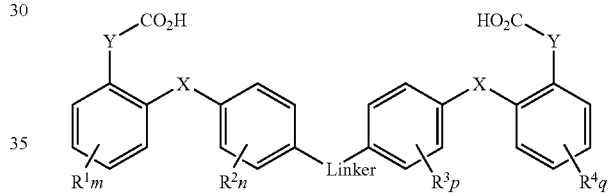

wherein:
each Y is independently a direct bond or —CH$_2$—;
each X is independently —NH—, —O—, —S—, —CH$_2$—, —NR—, —CO—, —CONH—, —CONR—, —C=N—O—, —NHCO—, —NRCO—, —O—N=C—, —SO—, —SO$_2$— or a direct bond,
each of R$^1$, R$^2$, R$^3$ and R$^4$ is independently F, Cl, Br, I, CF$_3$, OCF$_3$, R', OR', NR'R', SOR' or SO$_2$R',
wherein R and R' are each independently C$_1$-C$_3$ alkyl which is straight or branched chain or cyclic optionally substituted by one or more halogen atoms;
and each m, n, p and q is independently 0 to 4, wherein m+n+p+q>0;
and wherein the linker is a linear or branched chain of 7 to 13 carbon atoms, such as C$_7$-C$_{13}$ alkyl, C$_7$-C$_{13}$ alkenyl, C$_7$-C$_{13}$ alkynyl, or which may have one or more of its carbon atoms optionally replaced by a heteroatom such as N, O, or S, wherein the said chain is unsubstituted or substituted by one or more groups comprising halogen, O, or N atoms, or OH, C$_1$-C$_3$ alkyl, C$_2$-C$_3$ alkenyl, C$_2$-C$_3$ alkynyl or C$_1$-C$_3$ alkoxy.

The invention also encompasses any stereoisomer, enantiomer or geometric isomer, and mixtures thereof.

In the present patent application, including the accompanying claims, the aforementioned substituents have the following meanings:
Halogen atom means fluorine, chlorine, bromine or iodine.
Alkyl groups and portions thereof (unless otherwise defined) may be a straight or branched chain.

The term "$C_1$-$C_3$ alkyl" as used here refers to a straight or branched chain or cyclic carbon chain consisting of 1 to 3 carbon atoms, which can be optionally substituted by one or more halogens.

The term "$C_2$-$C_3$ alkenyl" as used here refers to a chain consisting of 2 to 3 carbon atoms, which contains one double bond which can be located in any position of the respective unsaturated radical and can be optionally substituted by one or more halogen atoms.

The term "$C_2$-$C_3$ alkynyl" as used here refers to a chain consisting of 2 to 3 carbon atoms, which contains one triple bond which can be located in any position of the respective unsaturated radical and can be optionally substituted by one or more halogen atoms.

The term "$C_1$-$C_3$ alkoxy" as used here refers to a straight or branched or cyclic carbon chain consisting of 1 to 3 carbon atoms, which is connected via oxygen atom to another group.

The term "$C_7$-$C_{13}$-alkyl" as used herein refers to a saturated straight or branched hydrocarbon saturated chain consisting of 7 to 13 carbon atoms.

The term "$C_7$-$C_{13}$-alkenyl" as used herein refers to an unbranched or branched non-cyclic carbon chain consisting of 7 to 13 carbon atoms, which contains at least one double bond which can be located in any position of the respective unsaturated radical.

The term "$C_7$-$C_{13}$-alkynyl" as used herein refers to an unbranched or branched non-cyclic carbon chain consisting of 7 to 13 carbon atoms, which contains at least one triple bond which can be located in any position of the respective unsaturated radical.

When the $C_7$-$C_{13}$-alkyl, $C_7$-$C_{13}$-alkenyl or $C_7$-$C_{13}$-alkynyl groups comprises one or more heteroatoms, the heteroatoms can be arranged in the said chain at any position or at the ends of the chain so that they connect the said chain to the phenyl radicals and the said chain can be unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In one embodiment of the invention, the heteroatom is not arranged at the end of the linker chain. In another embodiment of the invention, the heteroatom is oxygen.

In a second aspect, there is provided an agent for stabilising the tetrameric form of transthyretin, which comprises a compound of the general formula (I) or a pharmaceutically acceptable salt, ester or prodrug thereof in which:

each Y is a direct bond;
each X is independently —NH—, —NR—, —CO—, —CONH—, —CONR—, —NHCO—, —NRCO—, or a direct bond,
each of $R^1$, $R^2$, $R^3$ and $R^4$ is independently F, Cl, $CF_3$, $OCF_3$, R', OR', NRR', SOR' or $SO_2R'$,
wherein R and R' are each independently $C_1$-$C_3$ alkyl which is straight or branched chain or cyclic optionally substituted by one or more halogen atoms;
and each m, n, p and q is independently 0 to 4, wherein m+n+p+q>0;
and wherein the linker is a linear or branched chain of 7 to 13 carbon atoms, such as $C_7$-$C_{13}$ alkyl, $C_7$-$C_{13}$ alkenyl, $C_7$-$C_{13}$ alkynyl, or which may have one or more of its carbon atoms optionally replaced by a heteroatom such as N, O, or S, wherein the said chain is unsubstituted or substituted by one or more groups comprising halogen, O, or N atoms, or OH, $C_1$-$C_3$ alkoxy, $C_1$-$C_3$ alkyl, $C_2$-$C_3$ alkenyl, or $C_2$-$C_3$ alkynyl.

It has surprisingly been found that compounds according to the present invention potently stabilise the tetrameric transthyretin molecule. The compounds are rapidly and specifically bound with high affinity and avidity by native tetrameric transthyretin and remarkably occupy simultaneously both of the ligand binding pockets. Under physiological conditions of solvent pH, ionic strength and composition, the compounds are very rapidly bound, both by isolated pure transthyretin and by transthyretin in whole plasma, and displace thyroid hormone from its binding pocket in transthyretin. The compounds are bound such that each ligand occupies one of the binding pockets and the linker runs through the core of the transthyretin molecule. Such binding markedly stabilises the tetrameric assembly and native fold of transthyretin, and prevents the dissociation and misfolding which causes amyloid fibril formation. Furthermore binding of the compounds in this way by native transthyretin in whole plasma means that they are greatly superior as drugs compared with the compounds of the prior art.

Because m+n+p+q>0, at least one of the phenyl rings of die agent of the present invention must be substituted with a substituent selected from $R^1$, $R^2$, $R^3$ and $R^4$.

It is preferred that substitution takes place on at least one of the phenyl rings linked to the linker (i.e. those bearing $R^2$ and $R^3$), preferably whereby m=q=0.

It is preferred that n=p>0 so that both of these rings have the same number of substituents. More preferably n=p=2 so that the phenyl rings linked to the linker are disubstituted, most preferably meta disubstituted relative to X.

Substituents $R^2$ and $R^3$ are preferably each independently I, Br, Cl or F, most preferably Cl. It has surprisingly been found that the rings bearing $R^2$ and $R^3$ occupy the inner binding cavity of the transthyretin binding pockets contrary to the teaching of the prior art. According to this orientation, the l is situated in the central channel that runs through the transthyretin tetramer.

The inner binding cavity includes residues Ser117, Thr118 and Thr119, which may interact with substituents $R^2$ and $R^3$ by Van der Waals interactions. Further details of the inner binding cavity are described below.

It is preferred that X is NH or —CONH—, although other bridging atoms or groups may be used as described above. It is also preferred that Y is a direct bond.

The linker is a linear or branched chain of 7 to 13 carbon atoms, such as $C_7$-$C_{13}$ alkyl, $C_7$-$C_{13}$ alkenyl, $C_7$-$C_{13}$ alkynyl, or which may have one or more of its carbon atoms optionally replaced by a heteroatom such as N, O, or S, wherein the said chain is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy. The linker functions to link together the two ligands so that each ligand is situated in a binding pocket of the transthyretin tetramer and the linker passes through the central channel. Accordingly, the chain length of the linker must be appropriate to permit binding of both ligands so as to stabilise the tetrameric form of the transthyretin. Too short a linker would not permit this stabilisation because the ligands would be unable to bind. Too long a linker would potentially enable the binding of one ligand to one binding pocket only. It is observed in the present application that a chain length of 13 atoms is less preferred than a chain length of 9 atoms because the chain length of 9 atoms allows a better fit of the two ligands in their respective binding pockets.

The linker may comprise a hydrocarbon chain optionally attached to each ligand by a heteroatom.

In another aspect, the linker may comprise a chain length of 8 to 12 atoms, such as $C_8$-$C_{12}$ alkyl, $C_8$-$C_{12}$ alkenyl, $C_8$-$C_{12}$ alkynyl or which may have one or more of its carbon atoms optionally replaced by a heteroatom such as N, O, or S, wherein the said chain is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In another aspect, the linker may comprise a chain length of 9 to 11 atoms, such as $C_9$-$C_{11}$ alkyl, $C_9$-$C_{11}$ alkenyl, $C_9$-$C_{11}$ alkynyl or which may have one or more of its carbon atoms optionally replaced by a heteroatom such as N, O, or S, wherein the said chain is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In another aspect, the linker may comprise a chain length of 7 atoms, such as $C_7$ alkyl, $C_7$ alkenyl, $C_7$ alkynyl or which may have one or more of its carbon atoms optionally replaced by a heteroatom such as N, O, or S, wherein the said chain is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In another aspect, the linker may comprise a chain length of 8 atoms, such as $C_8$ alkyl, $C_8$ alkenyl, $C_8$ alkynyl or which may have one or more of its carbon atoms optionally replaced by a heteroatom such as N, O, or S, wherein the said chain is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In another aspect, the linker may comprise a chain length of 9 atoms, such as $C_9$ alkyl, $C_9$ alkenyl, $C_9$ alkynyl or which may have one or more of its carbon atoms optionally replaced by a heteroatom such as N, O, or S, wherein the said chain is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In another aspect, the linker may comprise a chain length of 10 atoms, such as $C_{10}$ alkyl, $C_{10}$ alkenyl, $C_{10}$ alkynyl or which may have one or more of its carbon atoms optionally replaced by a heteroatom such as N, O, or S, wherein the said chain is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In another aspect, the linker may comprise a chain length of 11 atoms, such as $C_{11}$ alkyl, $C_{11}$ alkenyl, $C_{11}$ alkynyl or which may have one or more of its carbon atoms optionally replaced by a heteroatom such as N, O, or S, wherein the said chain is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In another aspect, the linker may comprise a chain length of 12 atoms, such as $C_{12}$ alkyl, $C_{12}$ alkenyl, $C_{12}$ alkynyl or which may have one or more of its carbon atoms optionally replaced by a heteroatom such as N, O, or S, wherein the said chain is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In another aspect, the linker may comprise a chain length of 13 atoms, such as $C_{13}$ alkyl, $C_{13}$ alkenyl, $C_1$-$C_3$ alkynyl or which may have one or more of its carbon atoms optionally replaced by a heteroatom such as N, O, or S, wherein the said chain is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In another aspect, the linker comprises —O—$(CH_2)_r$—O— in which r is an integer of from 5 to 11, for example, 7 to 11, and the said linker can have one or more of its $CH_2$ groups optionally replaced by a heteroatom such as N, O, or S, or one or more double or triple bond, and wherein the said linker is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In another aspect, the linker comprises —O—$(CH_2)_r$—O— in which r is an integer of from 5 to 11, for example, 7 to 11.

In another aspect, there is provided an agent for stabilising the tetrameric form of transthyretin, which comprises a compound of the general formula (I) or a pharmaceutically acceptable salt, ester or prodrug thereof in which:
each Y is a direct bond;
each X is independently —NH—, —NR, —CONH—, —CONR—, —NHCO—, —NRCO—, or a direct bond,
each of $R^1$, $R^2$, $R^3$ and $R^4$ is independently F, Cl, $CF_3$, $OCF_3$, R', or OR',
wherein R and R' are each independently $C_1$-$C_3$ alkyl which is straight or branched chain or cyclic optionally substituted by one or more halogen atoms;
and each m, n, p and q is independently 0 to 4, wherein m+n+p+q>0;
and wherein the linker comprises —O—$(CH_2)_r$—O— in which r is an integer of from 5 to 11, for example, 7 to 11, and the said linker can have one or more of its $CH_2$ groups optionally replaced by a heteroatom such as N, O, or S, or one or more double or triple bond, and wherein the said linker is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In another aspect, there is provided an agent for stabilising the tetrameric form of transthyretin, which comprises a compound of the general formula (I) or a pharmaceutically acceptable salt, ester or prodrug thereof in which:
each Y is a direct bond;
each X is independently —NH—, —NR, —CONH—, —CONR—, —NHCO—, —NRCO—, or a direct bond,
each of $R^1$, $R^2$, $R^3$ and $R^4$ is independently F, Cl, $CF_3$, $OCF_3$, R', or OR',
wherein R and R' are each independently $C_1$-$C_3$ alkyl which is straight or branched chain or cyclic optionally substituted by one or more halogen atoms;
and each m, n, p and q is independently 0 to 4, wherein m+n+p+q>0;
and wherein the linker comprises —O—$(CH_2)_r$—O— in which r is an integer of from 5 to 11, for example, 7 to 11, wherein the said linker is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In a further preferred aspect of the present invention, there is provided an agent for stabilising the tetrameric form of transthyretin, which comprises a compound of the general formula (I) or a pharmaceutically acceptable salt, ester or prodrug thereof in which:
each Y is a direct bond;
each X is independently —NH—,
each of $R^1$, $R^2$, $R^3$ and $R^4$ is independently F or Cl,
and each m, n, p and q is independently 0 to 4, wherein m=q=0,
n=p=2 so that the phenyl rings linked to the linker are disubstituted, most preferably meta disubstituted relative to X, and wherein the linker comprises —O—$(CH_2)_r$O— in which r is an integer of from 5 to 11, for example, 7 to 11, wherein the said chain is unsubstituted or substituted by one or more groups comprising halogen, O, or N atoms, or OH, $C_1$-$C_3$ alkoxy, $C_1$-$C_3$ alkyl, $C_2$-$C_3$ alkenyl, or $C_2$-$C_3$ alkynyl.

In an additional aspect, the linker comprises —O—$(CH_2)_r$—O— in which r is 5, and the said linker can have one or more of its $CH_2$ groups optionally replaced by a heteroatom such as N, O, or S, or one or more double or triple bond, and wherein the said linker is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In an additional aspect, the linker comprises —O—$(CH_2)_r$—O— in which r is 6, and the said linker can have one or more of its $CH_2$ groups optionally replaced by a heteroatom such as N, O, or S, or one or more double or triple bond, and wherein the said linker is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In an additional aspect, the linker comprises —O—$(CH_2)_r$—O— in which r is 7, and the said linker can have one or more of its $CH_2$ groups optionally replaced by a heteroatom such as N, O, or S, or one or more double or triple bond, and wherein the said linker is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In an additional aspect, the linker comprises —O—$(CH_2)_r$—O— in which r is 8, and the said linker can have one or more of its $CH_2$ groups optionally replaced by a heteroatom such as N, O, or S, or one or more double or triple bond, and wherein the said linker is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In an additional aspect, the linker comprises —O—$(CH_2)_r$—O— in which r is 9, and the said linker can have one or more of its $CH_2$ groups optionally replaced by a heteroatom such as N, O, or S, or one or more double or triple bond, and wherein the said linker is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In an additional aspect, the linker comprises —O—$(CH_2)_r$—O— in which r is 10, and the said linker can have one or more of its $CH_2$ groups optionally replaced by a heteroatom such as N, O, or S, or one or more double or triple bond, and wherein the said linker is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

In an additional aspect, the linker comprises —O—$(CH_2)_r$—O— in which r is 11, and the said linker can have one or more of its $CH_2$ groups optionally replaced by a heteroatom such as N, O, or S, or one or more double or triple bond, and wherein the said linker is unsubstituted or substituted by one or more groups comprising halogen. O, or N atoms, or OH, $C_1$-$C_3$ alkyl, $C_2$-$C_3$ alkenyl, $C_2$-$C_3$ alkynyl or $C_1$-$C_3$ alkoxy.

Agents according to the present invention may be homobivalent compounds or heterobivalent compounds. groups such as tert-butyldimethylsilyl or methoxymethyl could also be utilized. This aniline material can be coupled to an aryl halide (which may be variously substituted around the arene ring as represented by $R^1m$ and may also be $R^4q$) by a palladium catalyzed coupling to afford an N-linked biaryl derivative. These materials may be O-deprotected to afford a phenol as a handle to enable the attachment of different linking groups. A range of different linkers can be attached though O-alkylation with dihalo-compounds (represented as X—R—X, where R is a chain length of 5 to 11 atoms as described above and X is halogen) to provide pharmaceutical agents of formula (I) wherein the linker comprises —O—$(CH_2)_r$—O— in which r is an integer of from 5 to 11, for example, 7 to 11, and the said linker can have one or more of its $CH_2$ groups optionally replaced by a heteroatom such as N, O, or S, or one or more double or triple bond, and wherein the said linker is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy. Further ester hydrolysis of the linked diester provides a compound of formula (I). Synthesis of other X-linked biaryl derivatives (as described above for the compound of formula (I)) can be achieved by well-known synthetic methods. Linkers comprising one or more double or triple bonds may be obtained through alkylation of commercially available alkene or alkyne building blocks such as trimethylsilylacetylene, and subsequent halogenation according to the procedures known to those skilled in the art. Other modes of attachment of the linker, such as direct attachment to the phenyl ring though carbon may be accomplished by, but are not limited to metal catalyzed cross-coupling reactions of a phenyl O-trifluoromethansulfonate derivative with dihalogenated compounds of formula X—R—X (wherein R is a chain length of 7-13 atoms). The generation of heterobivalent materials can also be accomplished through a modification of this procedure whereby stepwise attachment of the biphenyl units to dihalogenated compounds of formula X—R—X is employed. Linkers comprising heteroatoms such as N, O, or S and optionally substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy, may be prepared by methods known to those skilled in the art, include but are not limited to Mitsunobu reactions, standard amide- and ester-forming procedures, reductive amination, alkylation and acylation reactions, olefin metathesis.

Preferred agents according to the present invention include the compounds 4ajm15 and mds84, or a pharmaceutically acceptable salt, ester or prodrug thereof.

The present invention further provides a process for the preparation of a pharmaceutical agent.

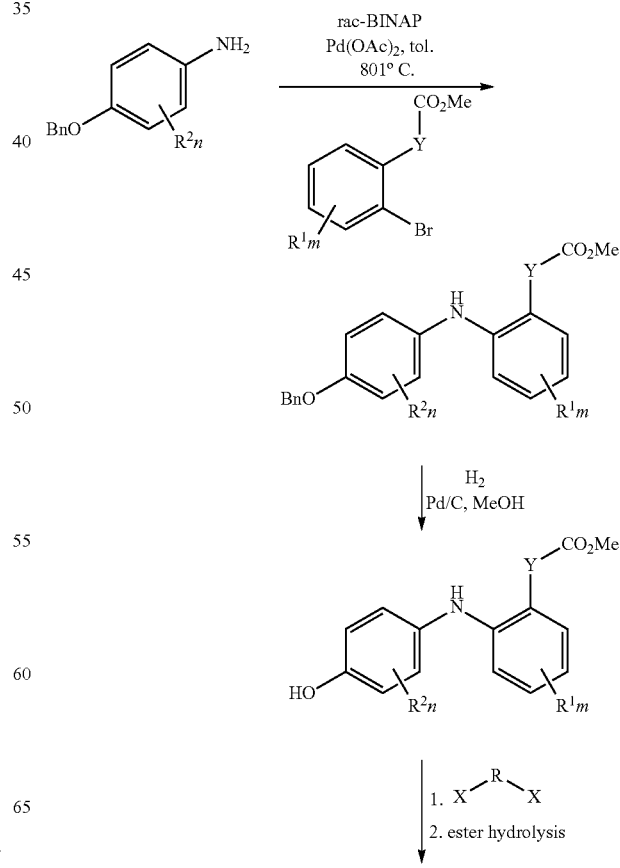

-continued

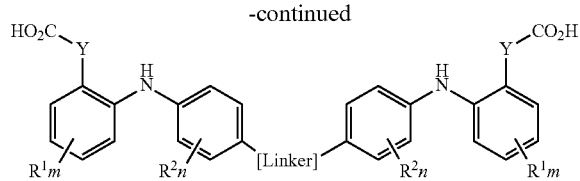

A general route for the generation of N-linked compounds of formula (I) may be exemplified by the scheme above.

A key building block is exemplified by a functionalized aniline (which may be variously substituted around the arene ring as represented by $R^2n$ and may also be $R^3p$) bearing an O-protected phenol. In the scheme above, a benzyl group is employed, but other O-protecting In a further aspect of the present invention, a process for the preparation of a pharmaceutical agent of formula (I) may be accomplished by coupling two molecules of formulas IIa and IIb to obtain a compound of formula (I). Substituents R' and R" represent the linker parts of various chain lengths to provide the linker comprising the chain of 7 to 13 atoms as described above under the coupling conditions known in the art. L' and L" may represent functional groups capable of participating in those coupling reactions, which include but are not limited to —COOH, —NH$_2$, —OH, Halogen, —COCl, —SO$_2$Cl, —COO(C$_1$-C$_3$)alkyl, —OCO(C$_1$-C$_3$) alkyl, NH(C$_1$-C$_3$)alkyl, —OSO$_2$—(C$_1$-C$_3$)alkyl, -tri(C$_1$-C$_3$) alkylsilyl, and CN.

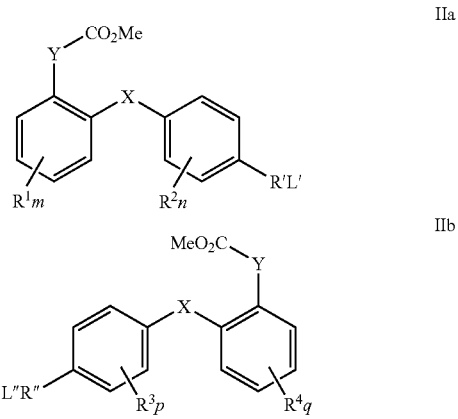

In a further aspect, the present invention provides an agent, as described herein, for use in the treatment or prevention of transthyretin amyloidosis, especially systemic transthyretin amyloidosis.

A method of treatment or prevention of transthyretin amyloidosis in a subject is also provided, which comprises administering to the subject a therapeutically effective amount of an agent as described herein to a subject in need of such treatment.

The types of amyloidosis treatable according to the present invention include senile cardiac transthyretin amyloidosis, autosomal dominant adult onset hereditary transthyretin amyloidosis, familial amyloid polyneuropathy of transthyretin type, and other disorders associated with transthyretin misfolding. The transthyretin by which the agents may be bound is wild type transthyretin or a variant form, including transthyretin having the single residue substitutions V30M, T60A, V122I or any of the other >80 different transthyretin variants which have been reported to cause transthyretin amyloidosis.

Pharmaceutical compositions may be formulated comprising an agent or a pharmaceutically acceptable salt, ester or prodrug thereof according to the present invention optionally incorporating a pharmaceutically acceptable carrier, diluent or excipient (including combinations thereof). By the term "pharmaceutically acceptable salt" is meant salts the anions or cations of which are known and accepted in the art for the formation of salts for pharmaceutical use. Acid addition salts, for example, may be formed by mixing a solution of the agent with a solution of a pharmaceutically acceptable, non-toxic acids, which include but are not limited to hydrochloric acid, oxalic acid, fumaric acid, maleic acid, succinic acid, acetic acid, citric acid, tartaric acid, carbonic acid or phosphoric acid. Where the agent carries a carboxylic acid group, the invention also contemplates salts thereof, preferably non-toxic, pharmaceutically acceptable salts thereof, which include, but are not limited to the sodium, potassium, calcium and quaternary ammonium salts thereof.

Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Antioxidants and suspending agents may be also used.

The pharmaceutical compositions may be in the form of a prodrug comprising the agent or a derivative thereof which becomes active only when metabolised by the recipient. The exact nature and quantities of the components of such pharmaceutical compositions may be determined empirically and will depend in part upon the route of administration of the composition. Where appropriate, the pharmaceutical compositions of the present invention can be administered by inhalation, in the folio of a suppository or pessary, topically (including ophthalmically) in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly, subcutaneously or intra-arterially.

For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of an agent, or a nontoxic, pharmaceutically acceptable salt thereof. The liquid forms in which the compositions of the present invention may be incorporated for administration orally or by injection include aqueous emulsions with edible oils such as cottonseed oil, sesame oil, coconut oil and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinyl-pyrrolidone and gelatin.

For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

For convenience of use, dosages according to the present invention are preferably administered orally but this will depend on the actual drug and its bioavailability.

Use of the compounds of the present invention aims to saturate with the ligand drug all circulating and other soluble transthyretin molecules in the body. The dose of drug required is therefore that which provides at least 1 mol of drug per mol of transthyretin produced each day. The daily production of transthyretin in normal healthy individuals is between 9.5 and 13 µmol/day in a 70 kg subject (Robbins J., 2002). There is no situation in which transthyretin production is upregulated and synthesis is reduced in all inflammatory, infective and tissue damaging diseases associated with an acute phase response and in malnutrition. For a compound of molecular mass 700 Da molar, equivalence with daily transthyretin production corresponds to 6.65-9.1 mg/day. If the drug were to be 100% bioavailable either orally or after parenteral administration then that dose range itself would be the minimum necessary. If the drug were given orally and was then, for example, just 10% bioavailable, the minimum daily dose would be ~70-100 mg. Depending on the exact affinity, pharmacokinetics and pharmacodynamics of the drug, the dose might need to be up to 1 g or more per day.

Pharmaceutically-acceptable salts include salts with a base or acid, which may be organic or inorganic. Salts of inorganic bases include those of alkali metals, alkaline earth metals and ammonium salts. Organic bases include pyridine, trimethylamine, triethylamine, and ethanolamine. Inorganic acids include hydrochloric acid, sulphuric acid, nitric acid and phosphoric acid. Organic acids include amino acids which may be basic or acidic, formic acid, acetic acid, citric acid, tartaric acid, fumaric acid and oxalic acid.

The precise form of pharmaceutical composition and dosage thereof may also be dependent on the subject to be treated, including body weight, route of administration and disease conditions. These would be determined as a matter of routine by the skilled addressee.

The invention will now be described in further detail, by way of example only, with reference to the accompanying drawings, in which:

FIG. 3 shows (A) results of SDS-PAGE analysis of transthyretin immunoprecipitates incubated with 4ajm15, and (B) displacement of T4 from transthyretin by 4ajm15 in whole serum;

DETAILED DESCRIPTION OF THE INVENTION

1. Wild Type Transthyretin 1.1 Purification. Native tetrameric transthyretin was purified from fractionated human plasma as previously described (Malpeli, 1996), obtained commercially (Scipac Ltd, Sittingbourne, Kent, UK), or produced by recombinant technology with isotopic labelling for the subunit exchange studies.

1.2 Mass spectrometric analysis. Mass spectrometric analyses were carried out on a Quattro II triple quadrupole mass spectrometer in either positive or negative ion electrospray modes. Samples were dissolved at 10-100 pmol/µl in acetonitrile:water:formic acid (1:1:0.01 v/v/v) or acetonitrile:water (1:1 v/v) for positive ion negative ion or mass spectrometric analysis respectively. Samples were introduced into the ion source at 10-20 µl/min using $N_2$ as nebulising gas. Spectra were reconstructed using Masslynx 4.0. Positive ion electrospray mass spectrometric (ESMS) analysis of the isolated transthyretin showed a number of major components present with MAv 13715.2±0.2 ($^{10}C \rightarrow ^{10}G$), 13732.3±1.0 ($^{10}C \rightarrow ^{10}dHA$), 13777.0±2.1 ($^{13}M \rightarrow ^{13}M$—O), 13791.9±2.8 ($^{10}C$—S.SH), 13841.3±0.2 ($^{10}C$—S.$SO_3H$), 13880.2±0.7 ($^{10}C$—S.Cys). Minor components also included "native" transthyretin (13760.5), $^{10}C$—S.Cys.Gly (13939.7) and $^{10}C$—S.GSH (14066.3). These results are consistent with reported values.

Figure 1:
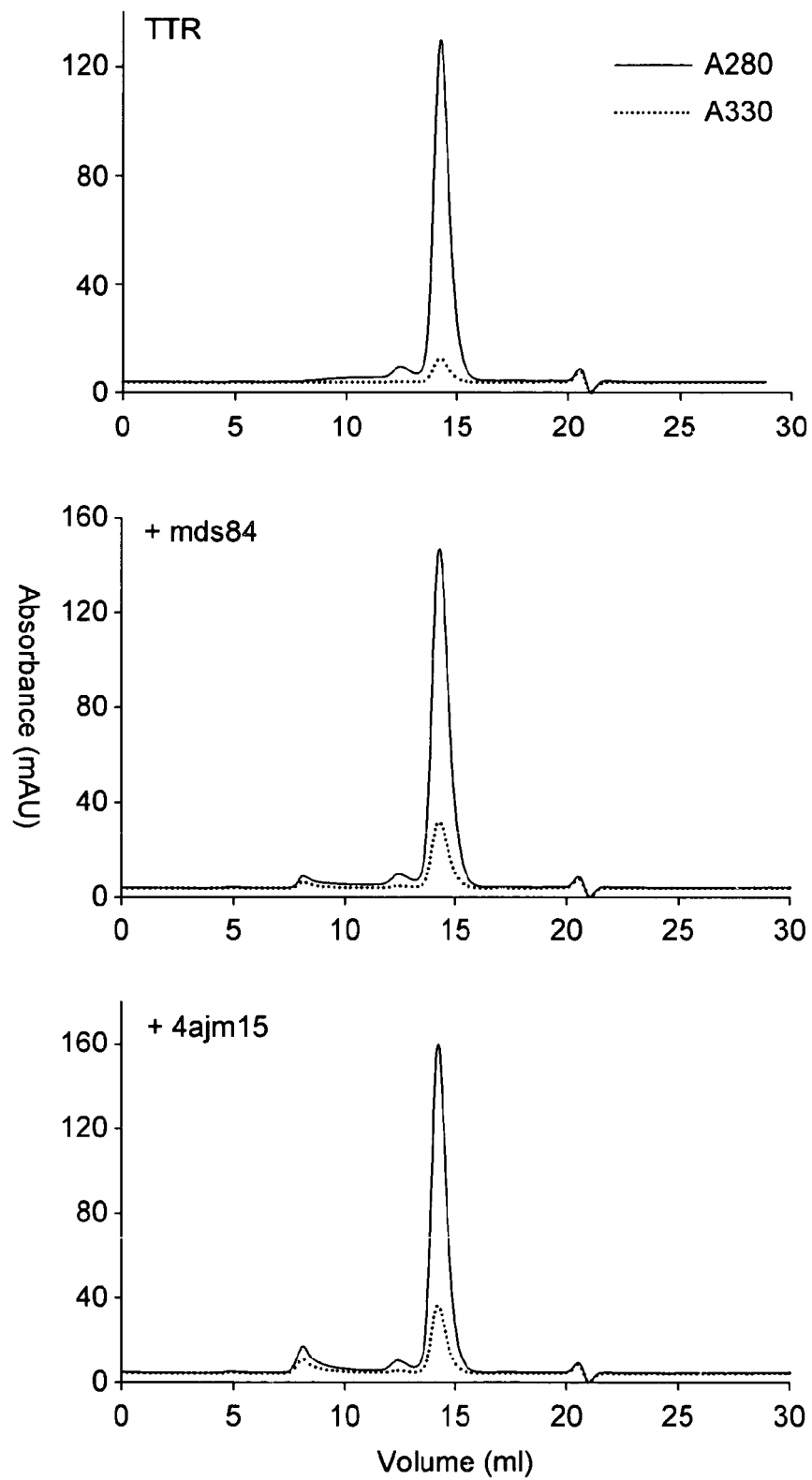
FIG. 1 shows size exclusion chromatography of transthyretin alone and complexed with 4ajm15 and mds84.

1.3 Gel filtration. Native transthyretin was eluted with either PBS or 150 mM ammonium bicarbonate (pH 7.6) from a Superdex 200 (30×1.0 cm) column, run on an ÄKTA Explorer system, as a UV absorbing peak ($A_{280}/A_{330}$~30 to 50:1) with $V_e$ 14.4 ml (FIG. 1). A minor (<5%) higher molecular weight component eluting at 12.5 ml was always seen.

1.4 Radioiodination. Isolated native wild type transthyretin purified from serum was oxidatively iodinated with $^{125}I$ (Reay, 1982). The specific activity was 0.44 MBq/pmol.

1.5 Desalting and buffer exchange. Biospin P6 columns (BioRad) were used according to the manufacturer's instructions. For buffer exchange the columns were washed four times centrifugally with the appropriate buffer.

2. Synthesis of Drugs and Ligands 2.1 Solvents and Reagents

THF was distilled under an atmosphere of dry nitrogen from lithium aluminium hydride and calcium hydride in the presence of triphenylmethane; DCM was distilled from calcium hydride; triethylamine was distilled from calcium hydride and stored over potassium hydroxide. Reactions performed under an atmosphere of hydrogen gas were maintained by an inflated balloon. Buffer at pH 7.0 was prepared by dissolving $KH_2PO_4$ (85 g) and NaOH (14.5 g) in distilled water (950 mL). All other reagents and solvents were used as supplied, without prior purification.

2.2 Chromatography

Thin layer chromatography (TLC) was performed on glass plates coated with Merck 60 $F_{254}$ silica and visualization was achieved by UV light or by staining with ceric ammonium molybdate or potassium permanganate. Flash column chromatography was carried out using Merck Kieselgel (230-400 mesh).

2.3 Nuclear Magnetic Resonance Spectroscopy

NMR spectra were recorded on a Bruker Avance 400 ($^1$H: 400 MHz and $^{13}$C: 100 MHz), or Bruker Avance Cryo 500 ($^1$H: 500 MHz and $^{13}$C: 125 MHz). Chemical shifts are quoted in ppm and are referenced to the residual non-deuterated solvent peak, and are reported (based on appearance rather than interpretation) as follows: chemical shift δ/ppm (number of protons, multiplicity, coupling constant J/Hz, assignment) [br, broad; s, singlet; d, doublet; t, triplet; q, quartet; qui, quintet; sept, septet; m, multiplet].

2.4 Synthesis of 2,2'-(4,4'-(undecane-1,11-diylbis(oxy))bis(3,5-dichloro-4,1-phenylene))bis(azanediyl)dibenzoic acid (4ajm15) and 2,2'-(4,4'-(heptane-1,7-diyl)bis(oxy))bis(3,5-dichloro-4,1-phenylene))bis(azanediyl)dibenzoic acid (mds84)

2.4.1 Reaction Scheme

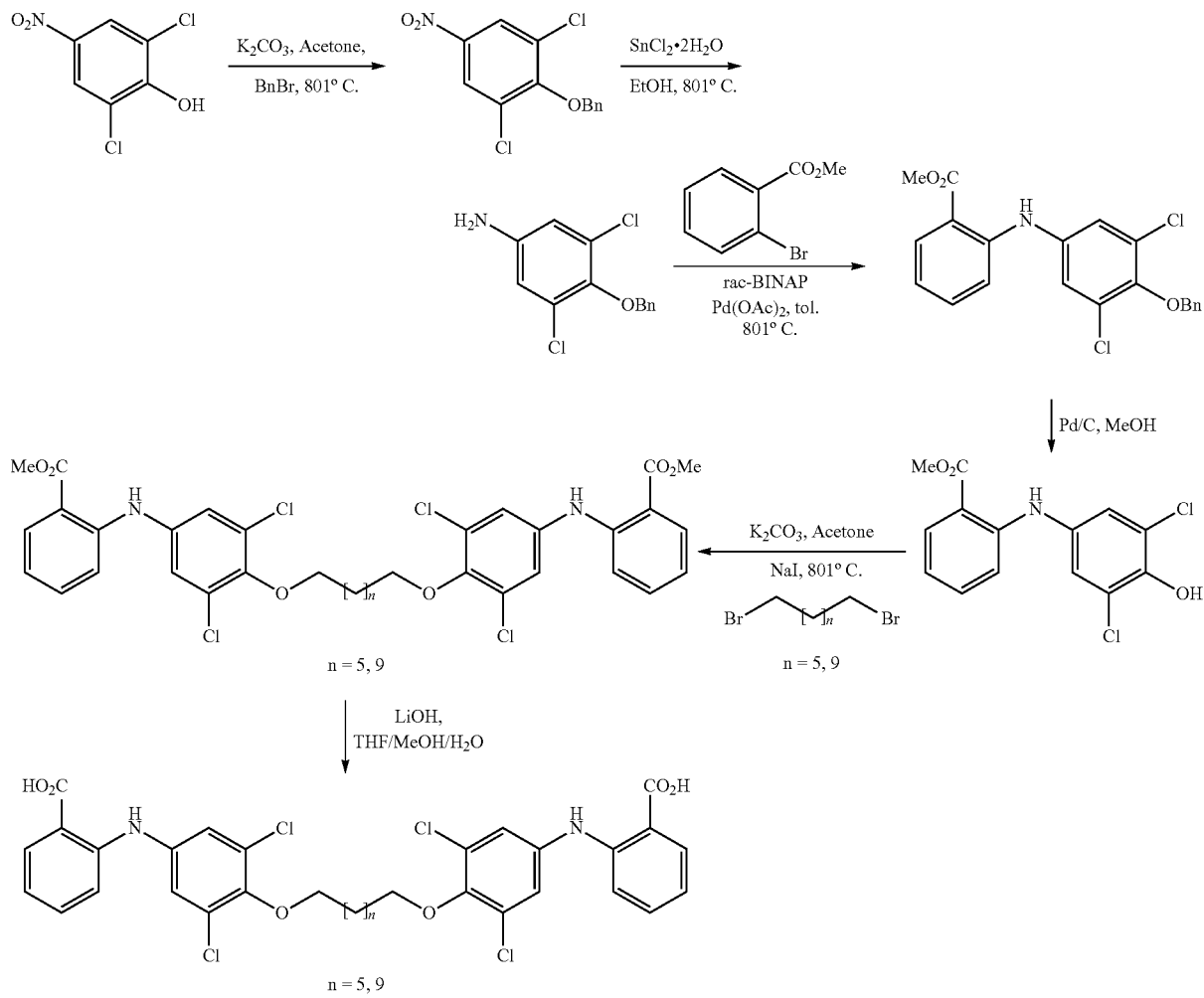

2.4.2 2-(Benzyloxy)-1,3-dichloro-5-nitrobenzene

Benzyl bromide (17.25 mL, 144 mmol) was added to a stirring solution of 2,6-dichloro-4-nitrophenol (5 g, 24 mmol) and potassium carbonate (13.3 g, 96 mmol) in acetone (30 mL). The mixture was heated to 75° C. for 12 h before being cooled to room temperature and poured into ice-water (100 mL). The mixture was extracted with chloroform (200 mL), washed with brine (100 mL) and the combined organic layers were dried (MgSO$_4$), filtered and concentrated in vacuo. The residue was purified by column chromatography (9:1, hexane/dichloromethane) to afford 2-(benzyloxy)-1,3-dichloro-5-nitrobenzene as a white solid (99% yield).

2.4.3 4-(Benzyloxy)-3,5-dichloroaniline

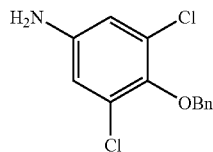

Tin(II) chloride (22 g, 98 mmol) was added to a stirring solution of 2-(benzyloxy)-1,3-dichloro-5-nitrobenzene (5.8 g, 19 mmol) in ethanol (80 mL), and the resulting suspension was heated to 70° C. After 1 h the mixture was cooled to room temperature and diluted with ethyl acetate (200 mL). The mixture was poured into brine (100 mL) and the resulting emulsion stirred with sodium potassium tartrate solution (200 mL). The mixture was extracted with ethyl acetate and the combined organic layers dried (MgSO$_4$), filtered and concentrated in vacuo to afford 4-(benzyloxy)-3,5-dichloroaniline that was used directly in the next step without purification.

2.4.4 Methyl 2-(4-(benzyloxy)-3,5-dichlorophenylamino)benzoate

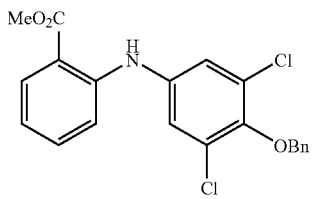

Cesium carbonate (5.98 g, 19 mmol) was added to a stirring solution of 4-(benzyloxy)-3,5-dichloroaniline (5.27 g [crude from previous step], 19 mmol) in toluene. Rac-BINAP (0.6 g, 7.5 mol %) and methyl 2-bromobenzoate (1.84 ml 13 mmol,) were added. Palladium(II) acetate (0.147 g, 5 mol %) was added and the mixture heated to 100° C. After 12 h the mixture was cooled to room temperature, diluted with ethyl acetate (100 mL), washed with pH 7 buffer solution (50 mL) and extracted with ethyl acetate (100 mL). The combined organic layers were dried (MgSO$_4$), filtered and concentrated in vacuo to afford a residue that was purified by column chromatography (3:1, petroleum ether/dichloromethane) to afford methyl 2-(4-(benzyloxy)-3,5-dichlorophenylamino) benzoate as a white solid (94% yield).

2.4.5 Methyl 2-(3,5-dichloro-4-hydroxyphenylamino)benzoate

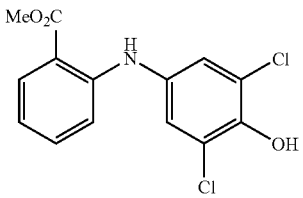

Palladium on carbon (10% by mass of 10% by wt Pd, 50 mg) was cautiously added to a deoxygenated stirring solution of methyl 2-(4-(benzyloxy)-3,5-dichlorophenylamino)benzoate (0.520 g, 1.3 mmol) in THF (15 mL). The mixture was subjected to three cycles of evacuation and purging with hydrogen gas, before being stirred under an atmosphere of hydrogen gas. After 3 h, the reaction was purged with nitrogen, filtered through Celite™ (eluent: THF) and concentrated in vacuo to afford methyl 2-(3,5-dichloro-4-hydroxyphenylamino)benzoate as a white solid that was used without further purification.

2.4.6 Dimethyl 2,2'-(4,4'-(heptane-1,7-diylbis(oxy)) bis(3,5-dichloro-4,1-phenylene))bis(azanediyl)dibenzoate

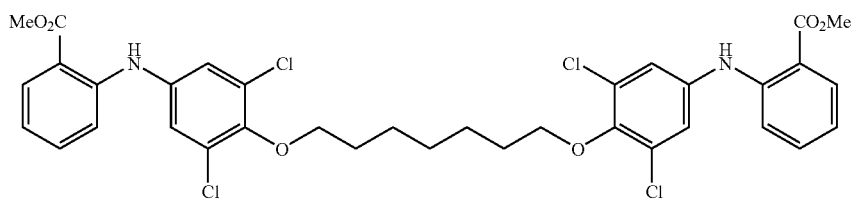

Dibromoheptane (0.088 mL, 0.54 mmol) was added to a stirring solution of methyl 2-(3,5-dichloro-4-hydroxyphenylamino)benzoate (0.426 g, 1.4 mmol) and potassium carbonate (1.4 g, 10.1 mmol) in acetone (3 mL) and the mixture was heated to 60° C. After 12 h, the mixture was cooled, diluted with dichloromethane (50 mL) and washed with pH 7 buffer solution (50 mL). The combined organic layers were dried (MgSO$_4$) filtered and concentrated in vacuo to give a residue that was purified by column chromatography (1:1, petroleum ether/dichloromethane) to afford dimethyl 2,2'-(4,4'-(heptane-1,7-diylbis(oxy))bis(3,5-dichloro-4,1-phenylene))bis (azanediyl)dibenzoate as a white solid (277 mg, 72% yield).

2.4.7 Dimethyl 2,2'-(4,4'-(undecane-1,11-diylbis(oxy))bis(3,5-dichloro-4,1-phenylene))bis(azanediyl)dibenzoate

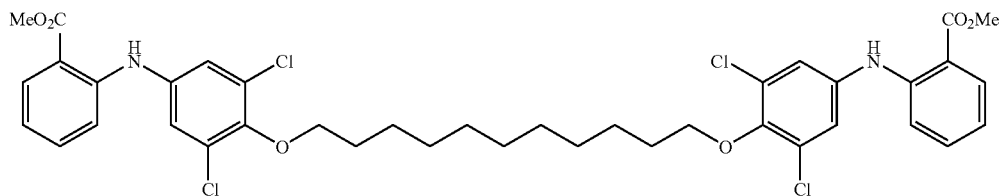

Dibromoundecane (0.133 mL, 0.56 mmol) was added to a stirring solution of methyl 2-(3,5-dichloro-4-hydroxyphenylamino)benzoate (440 mg, 1.41 mmol) potassium carbonate (0.390 g, 2.82 mmol) and tetra-N-butylammonium iodide (5 mg) in acetone (3 mL) and the mixture was heated to 60° C. After 12 h, the mixture was cooled, diluted with dichloromethane (50 mL) and washed with pH 7 buffer solution (50 mL). The combined organic layers were dried (MgSO$_4$) filtered and concentrated in vacuo to give a residue that was purified by column chromatography (1:1, petroleum ether/dichloromethane) to afford dimethyl 2,2'-(4,4'-(undecane-1,11-diylbis(oxy))bis(3,5-dichloro-4,1-phenylene))bis(azanediyl)dibenzoate as a white solid (408 mg, 94% yield).

2.4.8 2,2'-(4,4'-(heptane-1,7-diylbis(oxy))bis(3,5-dichloro-4,1-phenylene))bis(azanediyl)dibenzoic acid (mds84)

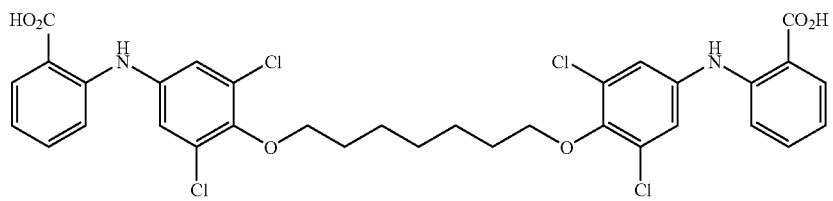

Methanol (1 mL) and water (1 mL) were added to a stirring solution of dimethyl 2,2'-(4,4'-(heptane-1,7-diylbis(oxy))bis(3,5-dichloro-4,1-phenylene))bis(azanediyl)dibenzoate (50 mg) in THF. Lithium hydroxide (25 mg) was added, and the mixture was stirred at room temperature for 14 h before being concentrated to approx. 2 mL. The solution was adjusted to pH 2 though addition of 3M aqueous HCl, and extracted with chloroform (50 mL). The organic layer was dried (MgSO$_4$), filtered and concentrated in vacuo to afford 2,2'-(4,4'-(heptane-1,7-diylbis(oxy))bis(3,5-dichloro-4,1-phenylene))bis(azanediyl)dibenzoic acid as an amorphous solid (48 mg, quantitative yield).

$\delta$H (400 MHz, (CD$_3$)$_2$CO): 8.03 (2H, dd, J 8.0, 1.3, H-3), 7.43-7.47 (2H, m, H-5), 7.28-7.34 (6H, m, H-10, H-4), 6.84-6.88 (2H, m, H-6), 4.04 (4H, at, J 6.4, H-14), 1.85-1.89 (4H, m, H-15), 1.58-1.65 (4H, m, H-16), 1.28-1.31 (2H, m, H-17).

2.4.9 2,2'-(4,4'-(undecane-1,11-diylbis(oxy))bis(3,5-dichloro-4,1-phenylene))bis(azanediyl)dibenzoic acid (4ajm15)

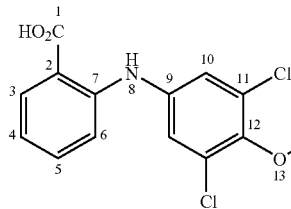
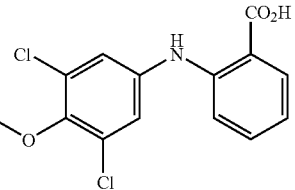

Methanol (1 mL) and water (1 mL) were added to a stirring solution of dimethyl 2,2'-(4,4'-(undecane-1,11-diylbis(oxy))bis(3,5-dichloro-4,1-phenylene))bis(azanediyl)dibenzoate (400 mg, 0.51 mmol) in THF. Lithium hydroxide (100 mg) was added, and the mixture was stirred at room temperature for 14 h before being concentrated to approx. 2 mL. The solution was adjusted to pH 2 though addition of 3M aqueous HCl, and extracted with chloroform (100 mL). The organic layer was dried ($MgSO_4$), filtered and concentrated in vacuo to afford 2,2'-(4,4'-(heptane-1,7-diylbis(oxy))bis(3,5-dichloro-4,1-phenylene))bis(azanediyl)dibenzoic acid as an amorphous solid (372 mg, 96% yield).

δH (500 MHz, $CDCl_3$): 7.92 (2H, dd, J 8, 1.6, H-3), 7.27-7.31 (2H, m, H-5), 7.25 (4H, s, H-10), 7.11-7.13 (2H, m, H-6), 6.70-6.74 (2H, m, H-4), 3.91 (4H, a-t, J 6.6, H-14), 1.73-1.79 (4H, m, H-15), 1.42-1.45 (4H, m, H-16), 1.25-1.30 (10H, m, H-17, H-18, H-19).

Synthesis of 2-(3,5-dichlorophenyl)benzo oxazole-6-carboxylic acid (FoldRx Pharmaceuticals, Inc., 300 Technology Square, Cambridge Mass. 02139, USA, compound Fx-1006A, CA: 594839-88-0), is given in WO 2004/056315; Razavi et al 2003; Razavi et al 2005.

3. Ligand Binding by Transthyretin
   3.1. Gel Filtration of Complexes of Transthyretin with 4ajm15 and mds84.
   3.1.1. Binding of 4ajm15 and mds84 by transthyretin. One µl (5.3 nmol) of a concentrated (5.3 mM) solution of 4ajm15 in DMSO was added to 3.8 nmol of transthyretin in 100 µl PBS (1.4 fold molar excess of ligand) and incubated at room temperature for 30 min. The sample was chromatographed on Superdex 200, where the transthyretin-4ajm15 complex eluted at 14.4 ml, with a reduced $A_{280}/A_{330}$ ratio (~5:1) consistent with binding. A similar result was obtained with transthyretin and 4ajm15 when chromatography was undertaken in volatile ammonium bicarbonate buffer. A similar result was also obtained when mds84 (2 nmol) was first dried into a tube and then resuspended in 5 µl of DMSO before adding the protein solution. In further experiments, 2 nanomoles of native wild type transthyretin (Scipac) were incubated in 55 µl of PBS for 1 h with either 1 µl DMSO (control) or 1 µl of a 4 mM solution in DMSO of mds84 or 4ajm15. Samples were chromatographed on a Superdex 200 column (30×1 cm) in PBS at 0.5 ml/min, with 0.5 ml fractions collected (FIG. 1). Transthyretin complexes with either mds84 of 4ajm15 showed a similar $A_{280}$ profile to transthyretin alone but the main component eluting at 14.4 ml exhibited increased absorbance at 330 nm ($A_{280}/A_{330}$ ratio ~4.6) demonstrating the presence of bound ligand. The full UV spectra of the main components were determined in each case and were consistent with a transthyretin:ligand ratio of ~1:0.9. In addition to indicating a mole for mole interaction of transthyretin with these ligands, the results importantly also show that the transthyretin-ligand complexes are stable after 100 volume solvent exchanges during gel filtration, with negligible dissociation of ligand from the complex.

Figure 2:
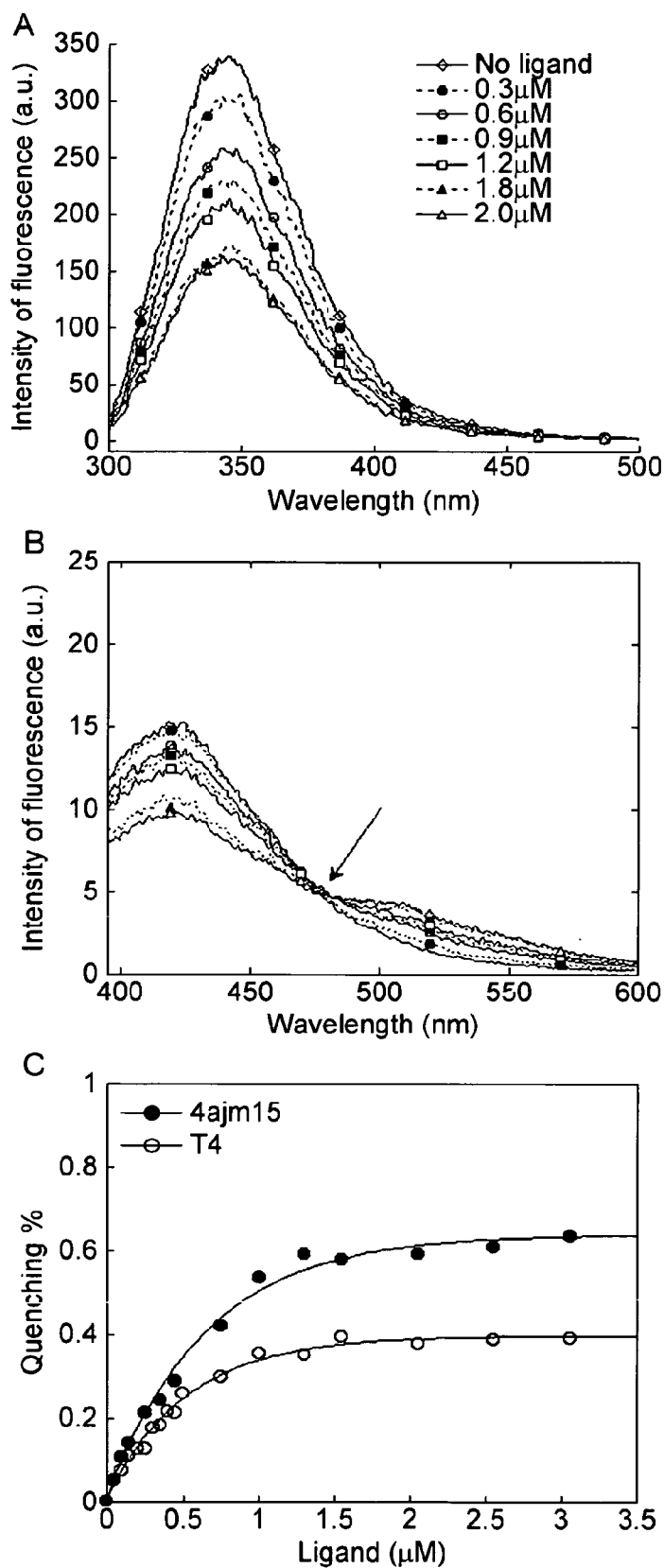
FIG. 2 shows (A) progressive transthyretin fluorescence quenching upon addition of 4ajm15, (B) comparison between 4ajm15 and T4 induced quenching and inset (a) fluorescence of 4ajm15 in presence of transthyretin.

3.2. Fluorescence Quenching.
   3.2.1. Binding of 4ajm15 and mds84 by transthyretin. The interactions between the ligands 4ajm15 or mds84 and transthyretin were studied by monitoring intrinsic fluorescence in the emission range 300-500 nm on excitation at 280 nm using a Perkin Elmer LS55 fluorimeter and a standard 1 cm path length quartz cell at 20° C. Quenching of tryptophan was achieved by titrating 1 µM transthyretin in PBS, pH 7.4 with increasing concentrations of each ligand in the range 0-2 µM (FIG. 2A). After titration with thyroxine (T4) transthyretin still exhibits 60% intrinsic fluorescence but this is reduced to only 40% by either of the novel ligands (FIG. 2C). At the same time the changes in 4ajm15 fluorescence upon binding to the protein were monitored in the emission range 400-600 nm and excitation at 340 nm that is the wavelength specific for 4ajm15 excitation. In these conditions, accumulation of the spectra highlights an isosbestic point at 483 nm (FIG. 2B). The same results were achieved by using mds84 (not shown). The results of the titration of 4ajm15 in presence and absence of transthyretin support a model of binding in which both the binding sites are simultaneously occupied by the palindromic ligand.

FIG. 2A shows the intrinsic fluorescence of transthyretin and 4ajm15 after excitation at 280 nm. FIG. 2B shows the emission spectra of transthyretin and 4ajm15 after excitation at 340 nm. In each case increasing concentrations of ligand (0-2 µM) were added to 1 µM protein. The arrow in FIG. 2B indicates the isosbestic point at 483 nm occurring on formation of the protein ligand complex. FIG. 2C shows titration curves of transthyretin at increasing concentrations of 4ajm15 and T4 plotted as % quenching of fluorescence versus ligand concentration. The percent quenching represents $\Delta F/F_0$ where $F_0$ is fluorescence intensity prior to the addition of ligands and ΔF is the decrease in fluorescence at a given ligand concentration.

3.2.2 Stopped flow analysis of the kinetics of 4ajm15 binding by transthyretin. The kinetics of transthyretin binding to 4ajm15 were evaluated with a Bio-Logic SFM-300 stopped flow device coupled to a fluorescence detection system (Claix, France) using a cell path length of 1.5 mm. The excitation wavelength was 280 nm and emission was measured at wavelengths greater than 320 nm using a cut off filter. The experiments were performed at 20° C. in PBS pH 7.4 containing 5% DMSO with a final protein concentration of 2 µM in the presence of 10 µM 4ajm15. The kinetic traces fit well to a single-exponential function with a time constant of 2.17 s (±0.02 s). Transthyretin thus binds 4ajm15 very rapidly at physiological pH with the plateau of the quenching reaction being reached after only ~11 sec.

3.2.3. Displacement of T4 from Isolated Transthyretin and in Whole Serum.

3.2.3.1 Quantitative studies on pure transthyretin. Competition of 4ajm15 or mds84 with T4 for binding by transthyretin was assayed quantitatively by a previously described procedure (Almeida et al., 1997; Saraiva et al., 1988). Their potency was also compared with Fx-1006A. Briefly, a solution of 125 nM transthyretin in 0.1 M Tris, 0.1 M NaCl and 0.001 M EDTA buffer, pH 8.0, was incubated with a trace amount of $^{125}$I-T4 plus increasing concentrations of inhibitor (0-10 μM) overnight at 4° C. $^{125}$I-T4 bound by transthyretin was separated from unbound T4 by gel filtration chromatography through a column of Bio-Gel P6-DG (Bio-Rad). Percentage binding was plotted against the logarithm of the inhibitor concentration, and the $IC_{50}$ (concentration of ligand reducing the binding of T4 by transthyretin by 50%) was determined (Table 1).

TABLE 1

$IC_{50}$ values for 4ajm15 and mds84 with respect to binding of T4 by wild type transthyretin isolated from plasma.

| Ligand | $IC_{50}$ (μM) |
| --- | --- |
| T4 | 0.1 ± 0.02 |
| 4ajm15 | 0.2 ± 0.07 |
| mds84 | 0.15 ± 0.025 |
| Fx-1006A | 0.59 |

3.2.3.2. Quantitative studies in serum. The displacement of T4 from transthyretin in whole serum, from individuals homozygous for wild type transthyretin and subjects heterozygous for various amyloidogenic transthyretin gene mutations, was studied by incubation of serum with $^{125}$I-T4 in the presence of 4ajm15 or mds84 at different molar concentrations followed by measurement of the radioactivity in the immunoprecipitate obtained with anti-transthyretin antibodies. Briefly 5 μl of serum were incubated overnight at 4° C. with 1 μl of $^{125}$I-T4 (specific radioactivity 1250 μCi/μg; concentration 320 μCi/ml; Perkin Elmer), 1 μl of 4ajm15 or mds84 at different molar concentrations and 33 μl of 0.1 M Tris, 0.1 M NaCl, 0.001 M EDTA, pH 8.0. $^{125}$I-T4 bound to transthyretin was separated from unbound T4 by gel filtration chromatography through a column of Bio-Gel P6-DG (Bio-Rad, Hercules, Calif., U.S.A.) loaded with 40 μl of the incubation mixture. The eluted proteins with bound T4 were incubated for 12 h at 4° C. with 10 μl of polyclonal anti-transthyretin antibody (DAKO) and 3% w/v PEG 6000. The immunoprecipitate was recovered by centrifugation, washed twice with 0.1 M Tris, 0.1 M NaCl, pH 8.0 and counted. Complete immunoprecipitation was confirmed by specific electroimmunoassay of transthyretin in the supernatants and the pellets were analysed by SDS 15% homogenous PAGE (GE Healthcare) (FIG. 3A). The $IC_{50}$ values (mean, SD μM) determined for 4ajm15 were: wild type transthyretin, 27.0, 4.9; transthyretin Ile122, 29.43, 4.8; transthyretin Ala60, 26.5, 7.2; transthyretin Tyr77, 26.2, 3.1; transthyretin Met30, 61.6, 1.6 (FIG. 3B). For mds84 the $IC_{50}$ for wild type transthyretin in serum was 11.88, 1.37. The mean $IC_{50}$ for Fx-1006A with wild type transthyretin in serum was 15.0 μM.

FIG. 3A shows the results of SDS-homogeneous 15% PAGE analysis of transthyretin immunoprecipitates after incubation of serum with $^{125}$I-T4 and 4ajm15 (lane 1, isolated transthyretin alone; lanes 2 to 13, immunoprecipitates at increasing concentrations of 4ajm15: 0, 0.069, 0.129, 0.259, 0.5, 1.03, 2.07, 4.15, 8.3, 16.6, 33.2 and 332 μM respectively). The corresponding supernatants of these samples were separated by native agarose gel electrophoresis and transferred to nitrocellulose membrane for detection by autoradiography. Lane 1 shows control native transthyretin pre-incubated with $^{125}$I-T4; lanes 2-13 show only bands corresponding to thyroxine binding globulin (TBG) with bound $^{125}$I-T4. FIG. 3B shows displacement of T4 from transthyretin by 4ajm15 in whole serum from individuals with wild type transthyretin and heterozygote carriers of various amyloidogenic variants.

3.2.3.3. T4 displacement from t4 binding proteins in the presence of transthyretin ligands. The distribution of the transthyretin ligand on T4 binding proteins in whole serum was evaluated by agarose gel electrophoresis (Jeppson et al, 1979) in the presence of $^{125}$I-T4 and increasing concentrations of ligand. After the electrophoresis, the proteins were transferred by capillary diffusion to a nitrocellulose membrane and subjected to phosphor imaging (Typhoon 8600; Molecular Diagnostics, Amersham Biosciences). The two known T4-binding proteins, transthyretin and thyroxine binding globulin (TBG), were distinctly visualized, while albumin binding appears as a radioactive smear between them. Densitometric analysis of the autoradiographic images clearly showed that increasing concentrations of 4ajm15 did not affect TBG binding of T4 by TBG, in contrast to the inhibition of binding by transthyretin.

3.3 Further In Vitro Binding Studies 3.3.1 Wild type transthyretin. The purified wild type transthyretin (liquid and lyophilised) used in these experiments, isolated from pooled normal human plasma, was obtained from Scipac, (Sittingbourne, Kent, UK). Protein concentration was determined by absorbance at 280 nm after correction for light scattering at 320 nm using the absorption coefficient $E_{1\ cm}^{1\%}=14.0$. In reducing denaturing conditions in SDS homogenous 15% PAGE (Amersham Biosciences, UK) stained with Brilliant blue R350, the transthyretin preparations migrated as a single major ~15 kDa band (monomer), although minor bands at ~36 and ~55 kDa, corresponding to dimers and SDS-resistant tetramers, were observed in heavily overloaded gels. Nano electrospray ionisation mass spectrometry confirmed the presence of normal and cysteinylated transthyretin monomers (Terazaki et al, 1998) under denaturing conditions, and solvent-bound transthyretin tetramer (Nettleton et al, 1998) under mild desolvation conditions.

Figure 4:
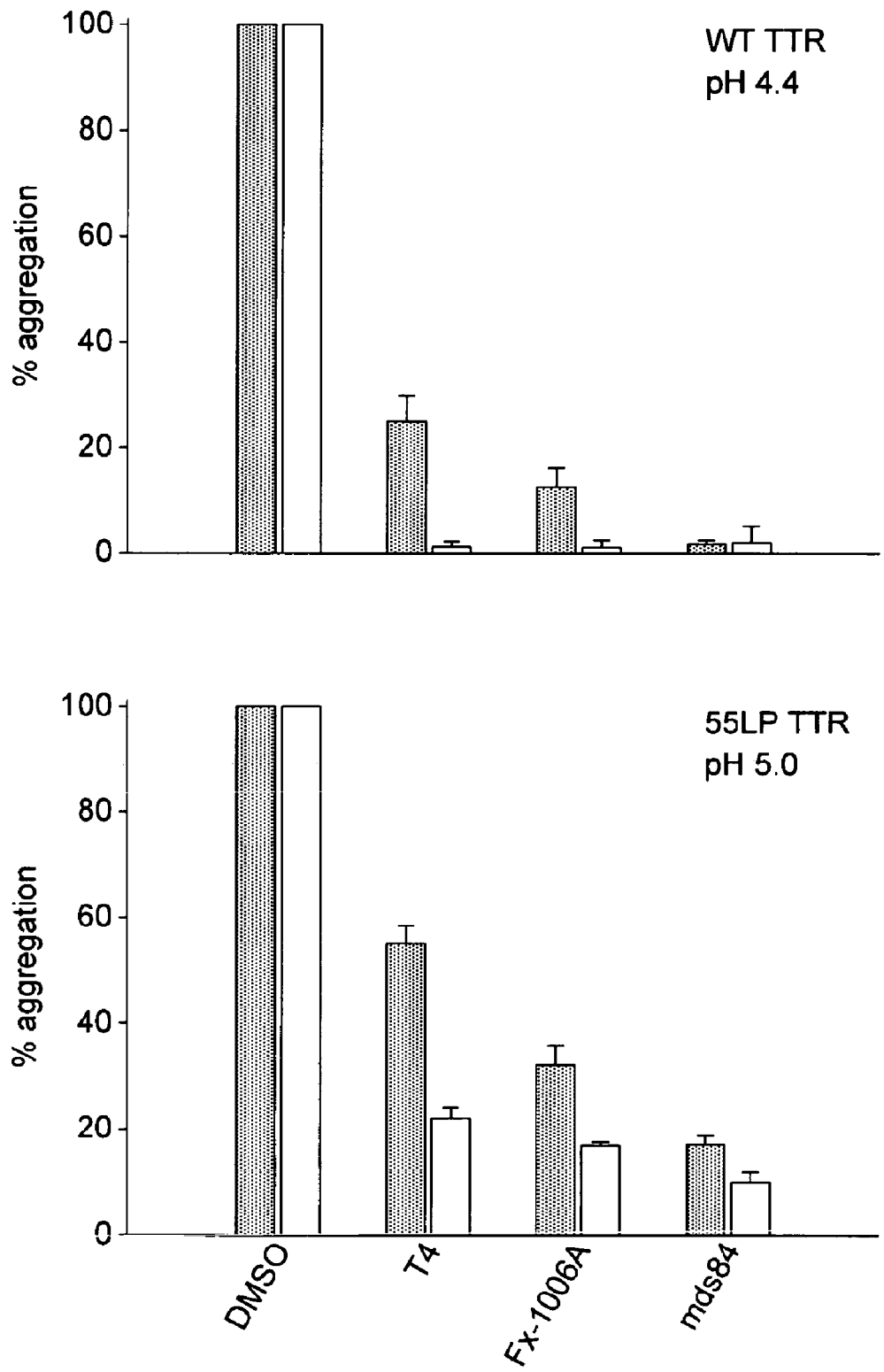
FIG. 4 shows transthyretin aggregate formation in presence of various transthyretin ligands.

3.3.2 Inhibition of transthyretin aggregation by 4ajm15: In pilot experiments, transthyretin aggregates were formed from wild type transthyretin (3.6 μM) after incubation at acidic pH for 3 d at 37° C. (Colon and Kelly, 1992). The efficacy of 4ajm15 as an inhibitor of transthyretin aggregate formation was then compared with other transthyretin ligand compounds. Briefly, aliquots of transthyretin (495 μl, 7.2 μM tetramer) in PBS buffer pH 7.4 (Sigma-Aldrich, Poole, UK) with 0.1% $NaN_3$ (PBS-az), were pre-incubated in triplicate with aliquots (5 μl, 72 mM) of 4ajm15 or control compounds (diclofenac, diflunisal, flufenamic acid and L-thyroxine [T4]), in DMSO (all Sigma-Aldrich), or DMSO alone. After 30 min at 37° C., the pH was adjusted to pH 4.4 (with 0.2 M sodium acetate buffer pH 4.0), and the ~1 ml mixtures were incubated unstirred for 3 d at 37° C. The absorbance of each sample was then measured at 21° C. in a UV-Vis scanning spectrophotometer (DU650; Beckman-Coulter UK Ltd, High Wycombe, Bucks) at 280, 320, 400 and 600 nm, after instrument blanking (PBS-acetate-DMSO), and results expressed as percentage turbidity (FIG. 4) and percentage inhibition of turbidity (Table 2), normalised to the $A_{400}$ nm value obtained for transthyretin without inhibitors (White and Kelly, 2001).

There was no appreciable absorbance at 400 nm attributable to transthyretin or any of the inhibitors tested individually at the concentrations used in the assay. In the presence of 4ajm15, transthyretin aggregate formation was dramatically reduced, presumably by stabilisation of the tetramer and prevention of its dissociation into monomers. Control inhibitors (NSAIDs, T4) yielded results that were consistent with those reported by others for this type of experiment (Miroy et al, 1996; Miller et al, 2004).

Using the same method the activities of mds84 and 4ajm15 as inhibitors of the aggregation of both wild type transthyretin and the most aggressively aggregating transthyretin variant, L55P, were evaluated in triplicate with both proteins at 3.6 µM and with one (3.6 µM) or 3 equivalents (10.8 µM) of each ligand. Wild type transthyretin was studied at pH 4.4 and L55P at pH 5.0. The inhibitory activity was also compared with the compound Fx-1006A and with T4. Mean values and standard deviations are shown in Table 2 and in FIG. 4, where results with 1:1 molar ratio are shown cross hatched and 3:1 molar ratio in open bars.

TABLE 2

Aggregation of transthyretin (per cent of control with DMSO alone)

| | wild type transthyretin | | | | 55LP variant transthyretin | | | |
|---|---|---|---|---|---|---|---|---|
| | Mean (1:1) | SD | Mean (3:1) | SD | Mean (1:1) | SD | Mean (3:1) | SD |
| DMSO | 100 | 0 | 100 | 0 | 100 | 0 | 100 | 0 |
| T4 | 25 | 4.8 | 1.2 | 0.94 | 55 | 3.4 | 22 | 2 |
| Fx-1006A | 12.5 | 3.7 | 1.14 | 1.3 | 32 | 3.8 | 16.8 | 0.7 |
| mds84 | 1.7 | 0.7 | 2 | 3 | 17 | 1.7 | 9.9 | 1.8 |

Wild type transthyretin aggregation is almost completely inhibited by the addition of 1 equivalent of mds84 (3.6 µM) while T4 and Fx-1006 produce the same level of inhibition only when 3 equivalents (10.8 µM) are added. The inhibitory effect of T4 has previously been reported to be maximal at three fold molar excess, at which T4 is bound in both the ligand binding pockets of the transthyretin tetramer (Miroy et al., 1996).

Aggregation of L55P variant transthyretin at pH 5.0 was similarly inhibited by mds84, which was also more potent than T4 or Fx-1006A at both molar equivalence and threefold molar excess. In tests with both wild type TTR and L55P, 4ajm15 produced results (not shown) that were identical to those with mds84.

Figure 5:
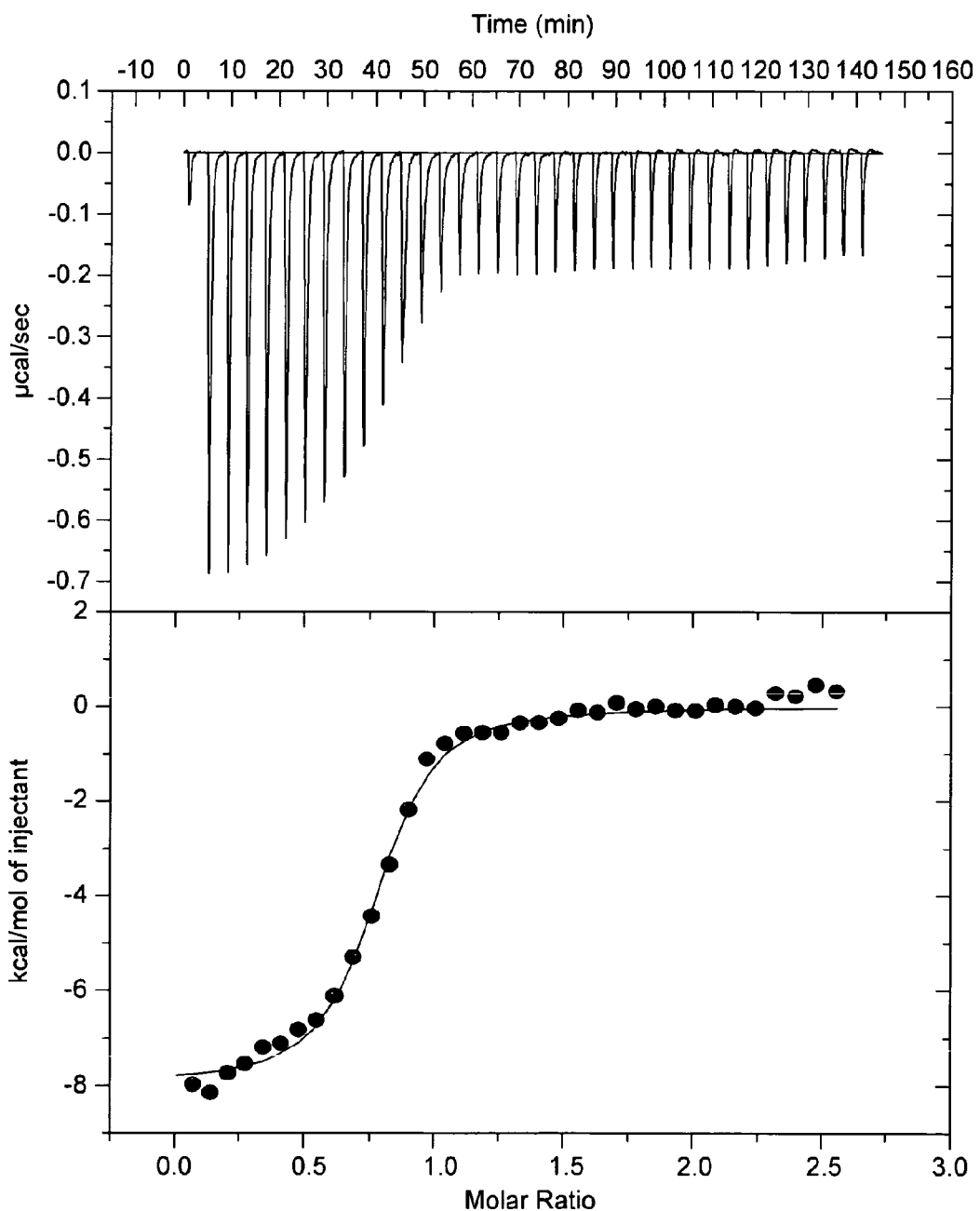
FIG. 5 shows isothermal titration calorimetry of binding of mds84 by transthyretin.

3.3.3 Isothermal titration calorimetry (itc) of transthyretin-mds84 ligand binding: Thermodynamic parameters of transthyretin-mds84 ligand binding were measured directly by isothermal titration calorimetry (VP-ITC, MicroCal LLC, Milton Keynes, UK). An initial injection of 1 µl of mds84 at 0.348 mM was made into transthyretin at a final concentration of 0.029 mM tetramer, followed, at 240 sec intervals, by 35 successive 8 µl injections. The diluent was Tris-NaCl pH 8.0 with 2% (v/v) DMSO. The sample cell was stirred at 310 rpm and cell contents were maintained at 37° C. After correction for volume displacement and plotting against the molar ratio of injected ligand to transthyretin tetramer, integration of the raw thermogram (FIG. 5, upper graph) yielded a binding isotherm (FIG. 5, lower graph) that was best fitted (determined by $\chi^2$ analysis) to a model with a single set of identical sites by non-linear least squares analysis in ORIGIN v7.0 (MicroCal LLC). The results yielded a dissociation constant ($K_d$; inverse of $K_a$) of 0.505 µM, enthalpy ($\Delta H$)=−7.95 kcal/mol and stoichiometry (n)=0.8 (~1:1). This analysis could not be performed with 4ajm15 due to its limited solubility.

3.3.4 differential scanning calorimetry (dsc) of transthyretin-4ajm15 ligand binding: Since 4ajm15 was too insoluble for analysis by ITC, preliminary differential scanning calorimetry (DSC) experiments were performed instead (VP-DSC MicroCal LLC; 0.02 mM transthyretin tetramer, temperature range 25-100° C., scan rate 1.5° C./min, cell pressure ~28 psi) in the presence and absence of 4ajm15 (0.2 mM). The diluent was PBS pH 7.4 with 2% DMSO. The midpoint of the thermal denaturation transitions ($T_m$) for transthyretin alone occurred at 99.5° C., but increased in the presence of 4ajm15 to 103.6° C., demonstrating binding of the ligand and consequent marked stabilisation of the protein. In further studies the effects of mds84 and Fx-1006A on Tm of wild type and L55P variant transthyretin were compared at five fold molar excess of ligand over protein. In the presence of mds84, the Tm of wild type transthyretin increased by 6.2° C., from 101.3° C. for transthyretin alone to 107.5° C. with the ligand. Fx-10006A caused a significantly smaller increase in Tm of 4.6° C., from 100.3° C. to 104.9° C. The L55P variant transthyretin melted at a lower temperature than wild type transthyretin but mds84 raised the Tm by 5.9° C., from 94.3° C. to 98.3° C., compared with a significantly smaller rise of 3.7° C., from 94.6° C. to 98.3° C. with Fx-1006A. These results demonstrate that mds84 is a more potent stabiliser than Fx-0006A for both wild type and variant transthyretin.

4. Stabilisation of Native Tetrameric Transthyretin by 4ajm15

4.1. Analytical ultracentrifugation. Sedimentation velocity and equilibrium analytical centrifugation experiments were performed at 20° C. on a Beckman XL-I instrument equipped with an An50Ti rotor in which both absorbance (recorded at a wavelength of 280 nm) and interference scans were recorded simultaneously. Sedimentation analyses were performed at pH 4.4 by incubating the protein (3.6 µM) for 72 h under the conditions of the stagnant transthyretin aggregation-inhibition assay (Petrassi et al., 2000) in presence of the ligand (3.6 µM). T4 dissolved in DMSO at the aggregation inhibiting concentration of 10.8 µM (Miroy et al., 1996) and DMSO alone were also incubated with the protein in the same conditions and analysed as controls. Sedimentation velocity data were acquired over 8 h at rotor speed of 42,000 rpm in two-sector cells with solution column heights of 12 mm. Absorbance values were modelled as a continuous distribution of sedimentation coefficients, c(s) (Schuck, 2000) using the software SEDFIT (Schuck, 2005). Sedimentation equilibrium measurements of transthyretin bound to the ligand, in the same conditions used for the sedimentation velocity analysis, were acquired using six-sector cells in an AnTi 50 rotor with column heights of 2 mm at rotor speed of 17,000 rpm until equilibrium was reached as shown by the perfect overlay of runs measured at intervals of 5 h. A final run at 42,000 rpm was performed at the end of the experiment to determine the background levels for use in curve fitting. Data analysis was performed using Beckman software provided as an add-on to Origin Version 4.1 (Microcal Inc.) for which the partial specific volume was calculated to be 0.7353 ml/g from the amino acid sequence (Perkins, 1986). The buffer density and viscosity were calculated using the program SEDNTERP (Laue et al., 1992). Sedimentation velocity and equilibrium analytical ultracentrifugation experiments were used to evaluate the influence of 4ajm15 on transthyretin quaternary structure under the conditions that typically dissociate the tetramer and make the monomer mis-assembly competent (72 h at 37° C. and pH 4.4). Under these conditions transthyretin which has bound 4ajm15 remains tetrameric and sediments as a single species (FIG. 6) with a sedimentation coefficient of 3.7 S comparable to that of transthyretin bound to its natural ligand (Miroy et al., 1996). More than one species were detectable in the control experiment performed in the presence of the solvent DMSO (inset FIG. 6). Sedimentation equilibrium analysis of transthyretin in the presence of the ligand was entirely consistent with a single species of mass 55,784±107.87 Da, in good agreement with the calculated molecular mass of tetrameric wild type transthyretin with bound 4ajm15 (55794 Da).

Figure 6:
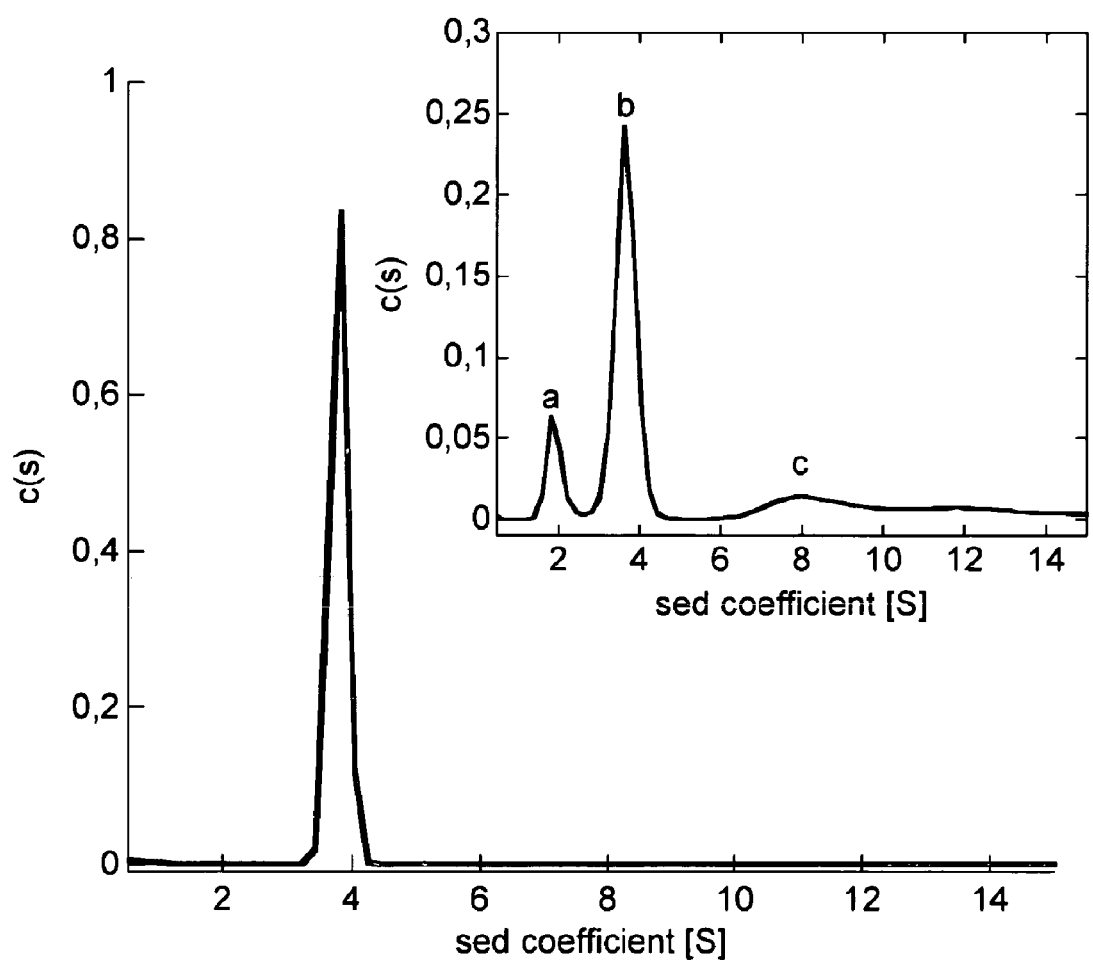
FIG. 6 shows variation of sedimentation velocity of transthyretin in presence and absence of 4ajm15.

FIG. 6 shows sedimentation velocity c(s) distribution of the complex transthyretin-4ajm15 under the conditions described above, displaying a single peak at 3.7 S corresponding to the expected S value of the tetramer. Under the same experimental conditions and in the absence of 4ajm15, transthyretin sediments as multiple species (inset) with S values corresponding to those expected for protomer (a), tetramer (b) and higher molecular species (c).

Figure 7:
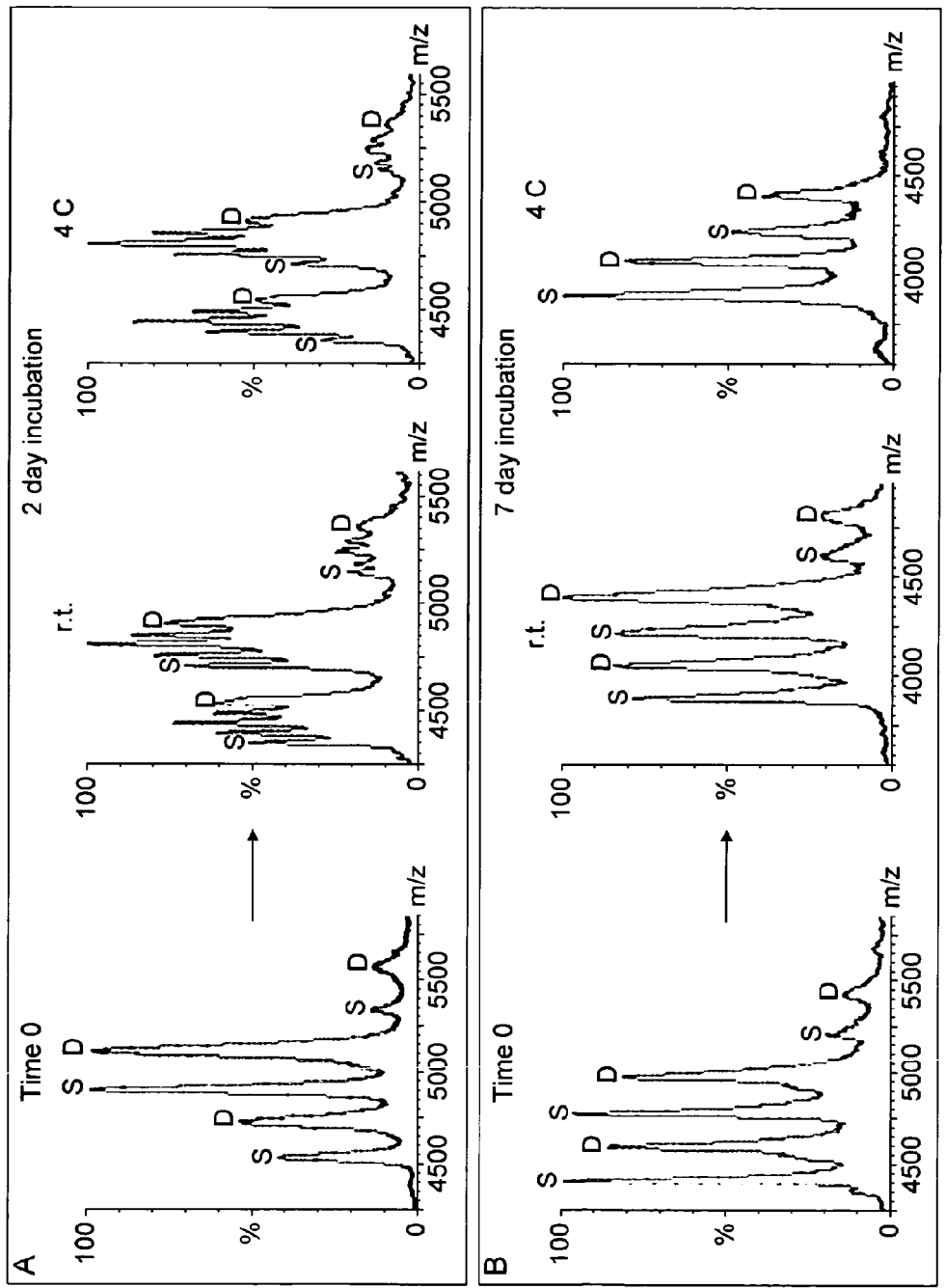
FIG. 7 shows mass spectra for a mixture of transthyretin synthetically labelled with $^{15}N$ and $^{13}C$, and with $^{15}N$ alone, in presence and absence of 4ajm15.

4.2 Mass spectrometric analysis of subunit exchange. Recombinant wild type, L55P and V30M transthyretin variants were biosynthetically labelled with isotopes [$^{15}$N] and [$^{15}$N, $^{13}$C] as previously described (Keetch C A et al, 2005). Immediately prior to analysis, proteins were buffer exchanged into 20 mM ammonium acetate, pH 7.0 using Micro Biospin columns (Bio-Rad, UK). The subunit composition of transthyretin was monitored as a function of time by incubating an equimolar solution (4.4 µM) of [$^{15}$N] and [$^{15}$N, $^{13}$C] labelled proteins in the presence of 2-fold molar excess of 4ajm15 in DMSO or 2.5% DMSO alone as a control. Each experiment was carried out in triplicate at room temperature and at 4° C. as well, since it is known that subunit exchange is accelerated at low temperatures. Nanoflow ESMS was performed on a QToF2 instrument (Waters/Micromass UK, Ltd.) modified for high mass operation (Sobott et al, (2002)) and calibrated externally using caesium iodide (100 mg/ml). Each solution, 1.5 µl, was electrosprayed from gold coated borosilicate capillaries prepared in-house as described (Nettleton E J, et al, 1998). To preserve the non-covalent interactions in the transthyretin tetramer, the MS parameters applied were: capillary voltage 1.6 kV, sample cone 160 V, extractor cone 20 V, ion transfer stage pressure $7.0 \times 10^{-3}$ mbar, quadrupole analyzer pressure $9.5 \times 10^{-4}$ mbar and ToF analyzer pressure $1.7 \times 10^{-6}$ mbar. Data were processed with MassLynx software (Waters/Micromass UK, Ltd.) and are presented with minimal smoothing and without background subtraction. The subunit exchange of wild type transthyretin, as reported in FIG. 7, shows that the 4ajm15 ligand prevents any subunit exchange occurring under native conditions and on a biologically relevant timescale (Scheider F et al, 2001). Exactly the same effect was observed with the variant V30M and L55P (data not shown).

FIG. 7 shows mass spectra acquired under non-dissociating MS conditions for [$^{15}$N] and [$^{13}$C, $^{15}$N] wild type transthyretin (4.4 µM) in the presence of DMSO (A) and a 2 fold excess of ligand (B). S, tetramer of 4×[$^{15}$N] monomers, D, tetramer of 4×[$^{13}$C, $^{15}$N] monomers. Mass spectra of the control sample recorded after two days at room temperature and 4° C. show marked subunit exchange and the almost complete absence of exchange after 7 days in presence of 4ajm15. Each spectrum of wild type transthyretin with ligand was also acquired under dissociating MS conditions confirming full binding of the ligand to transthyretin (not shown).

Figure 8:
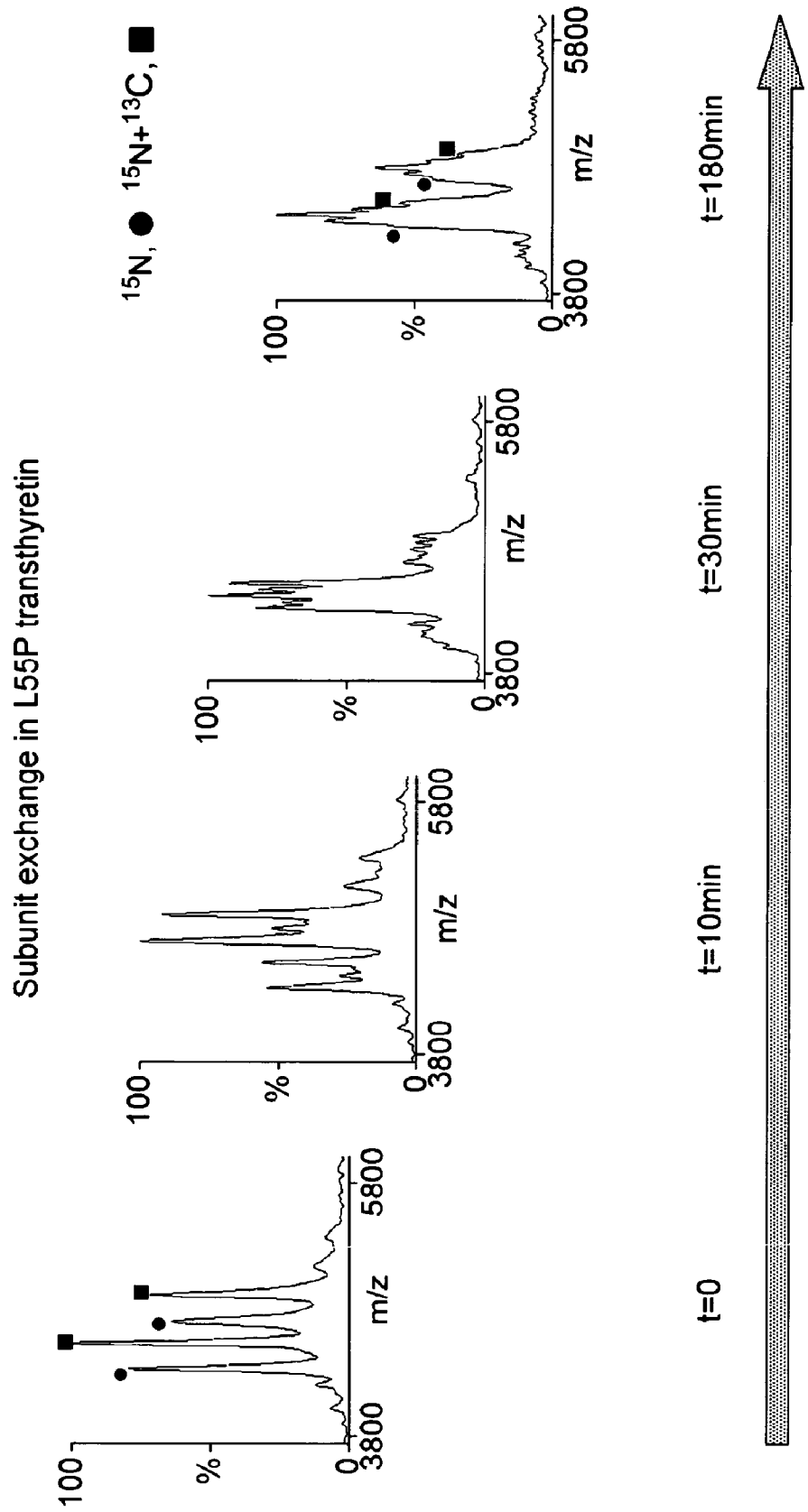
FIG. 8 shows mass spectra for a mixture of L55P variant transthyretin synthetically labelled with $^{15}N$ and $^{13}C$, and with $^{15}N$ alone.
Figure 9:
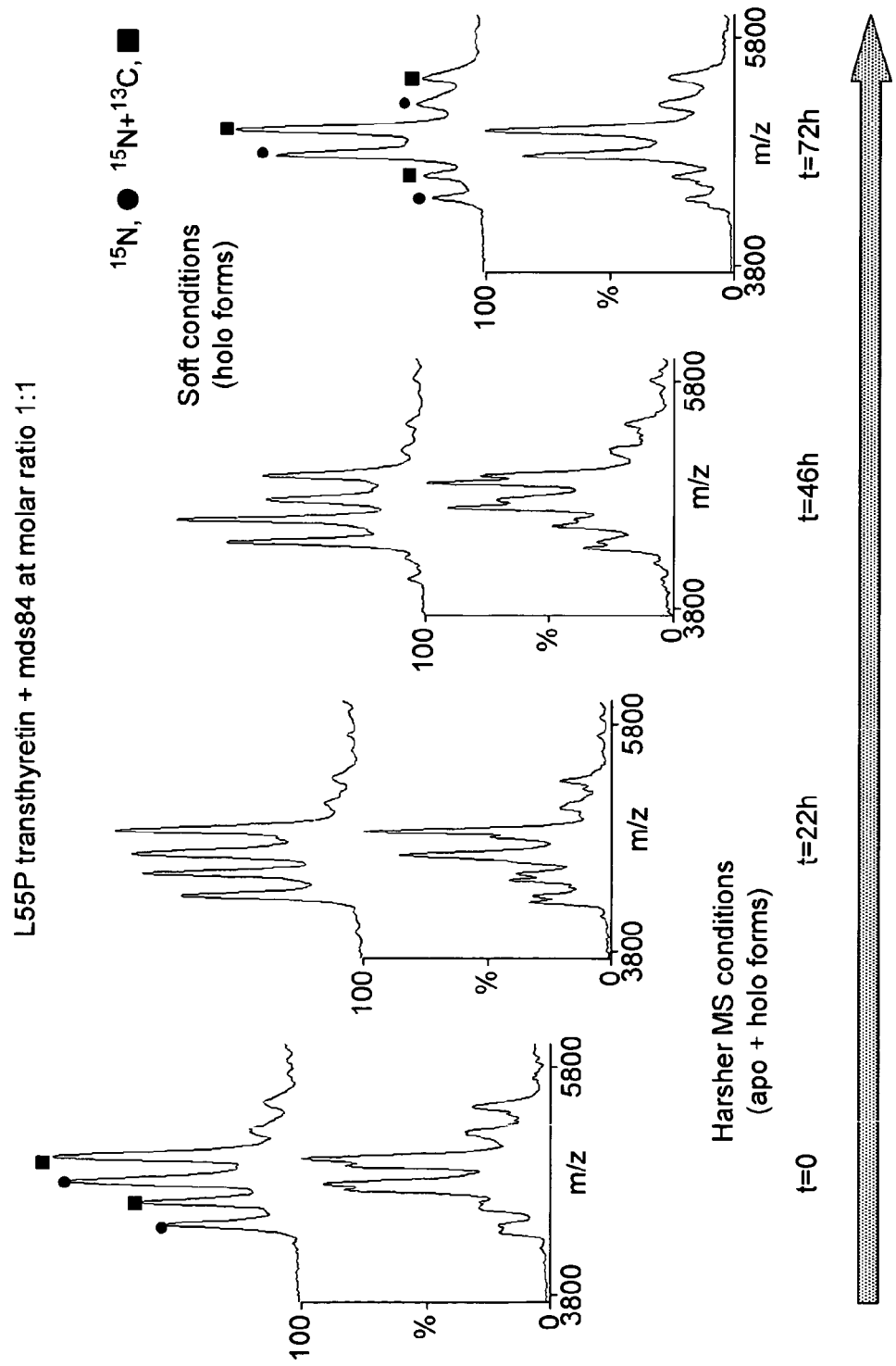
FIGS. 9, 10 and 11 show mass spectra for a mixture of L55P variant transthyretin synthetically labelled with $^{15}N$ and $^{13}C$, and with $^{15}N$ alone, together with different molar ratios of mds84.
Figure 10:
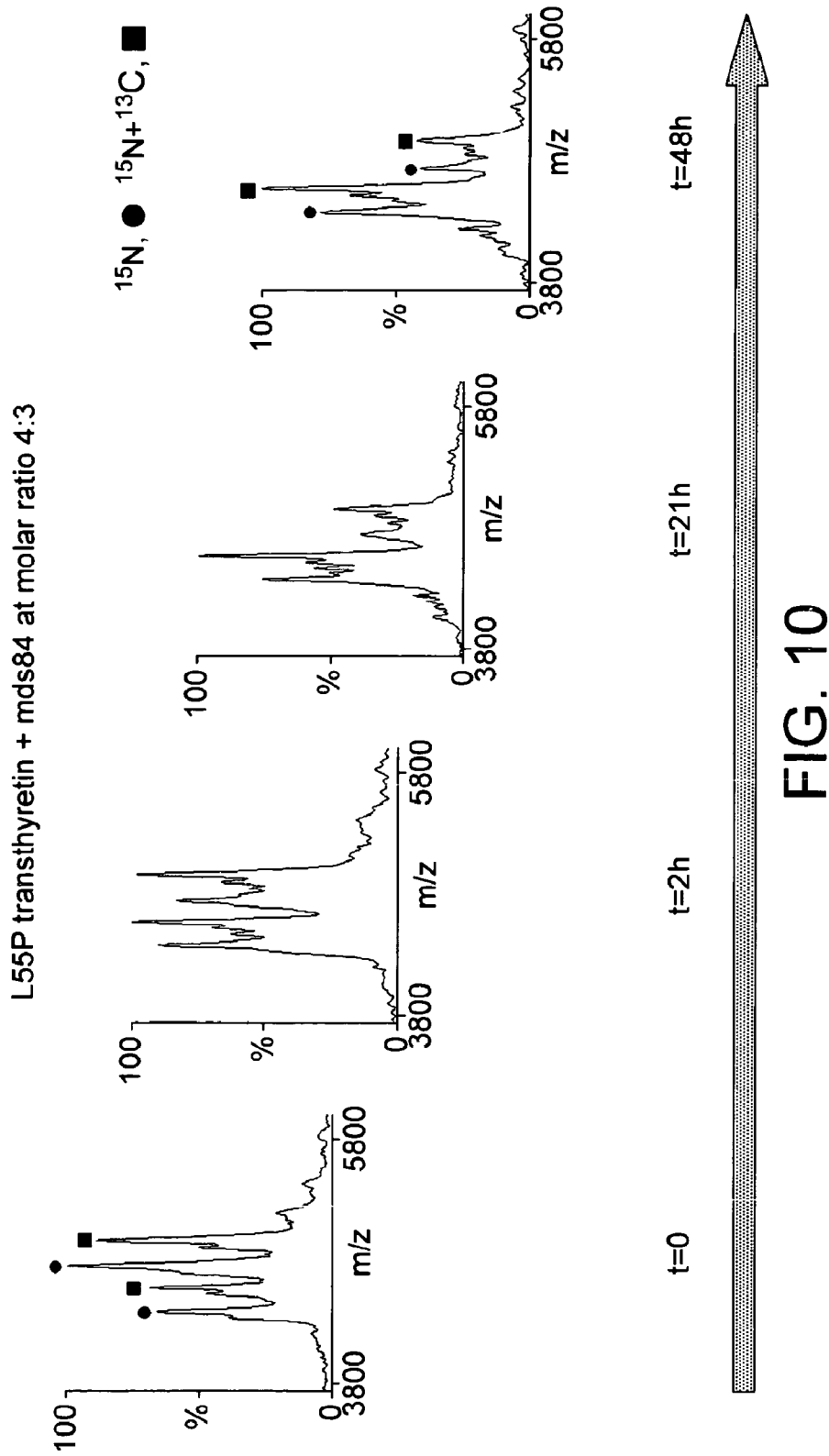
Figure 11:
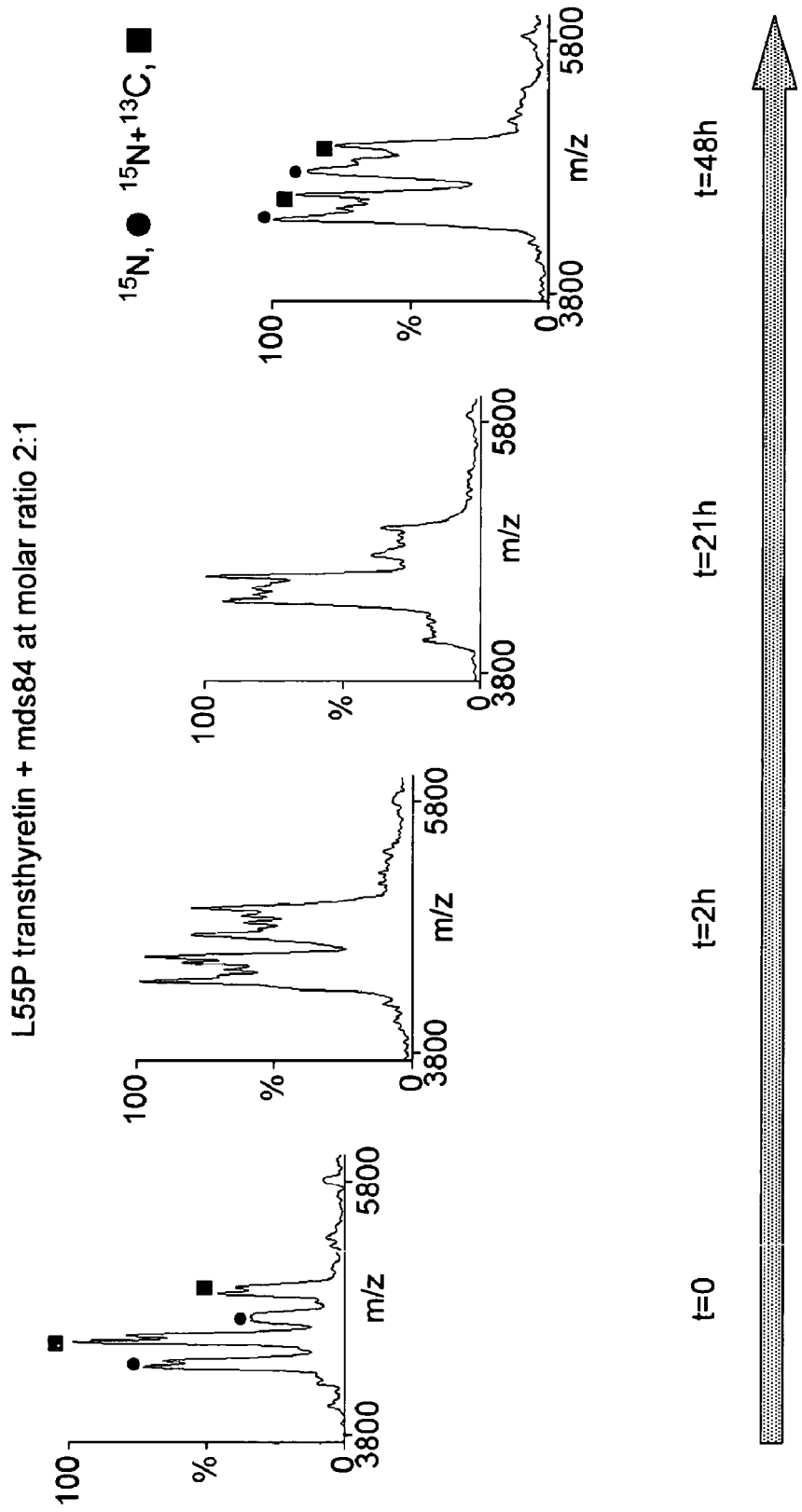
Figure 12:
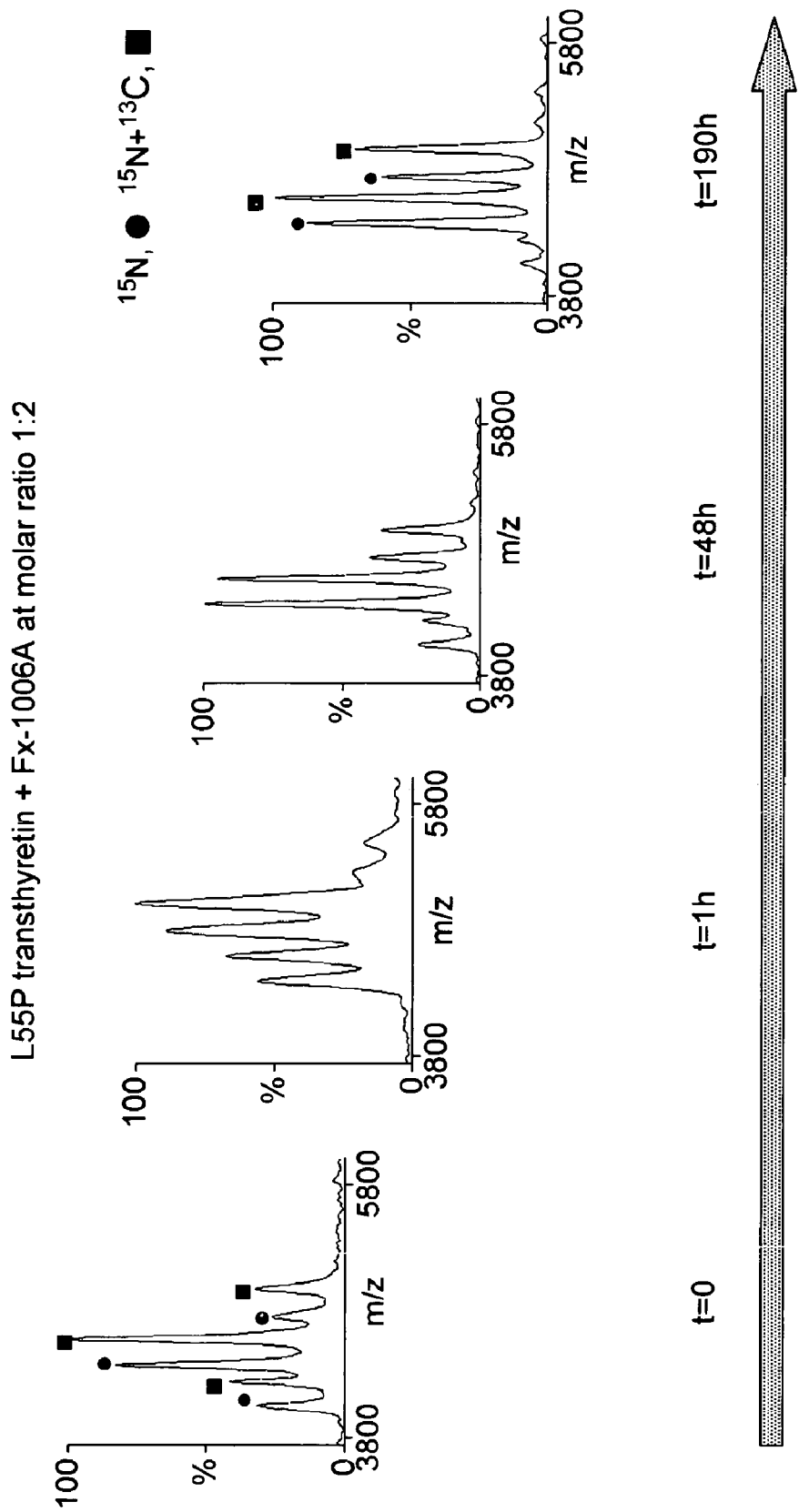
FIGS. 12, 13 and 14 show mass spectra for a mixture of L55P variant transthyretin synthetically labelled with $^{15}N$ and $^{13}C$, and with $^{15}N$ alone, together with different molar ratios of Fx-1006A.
Figure 13:
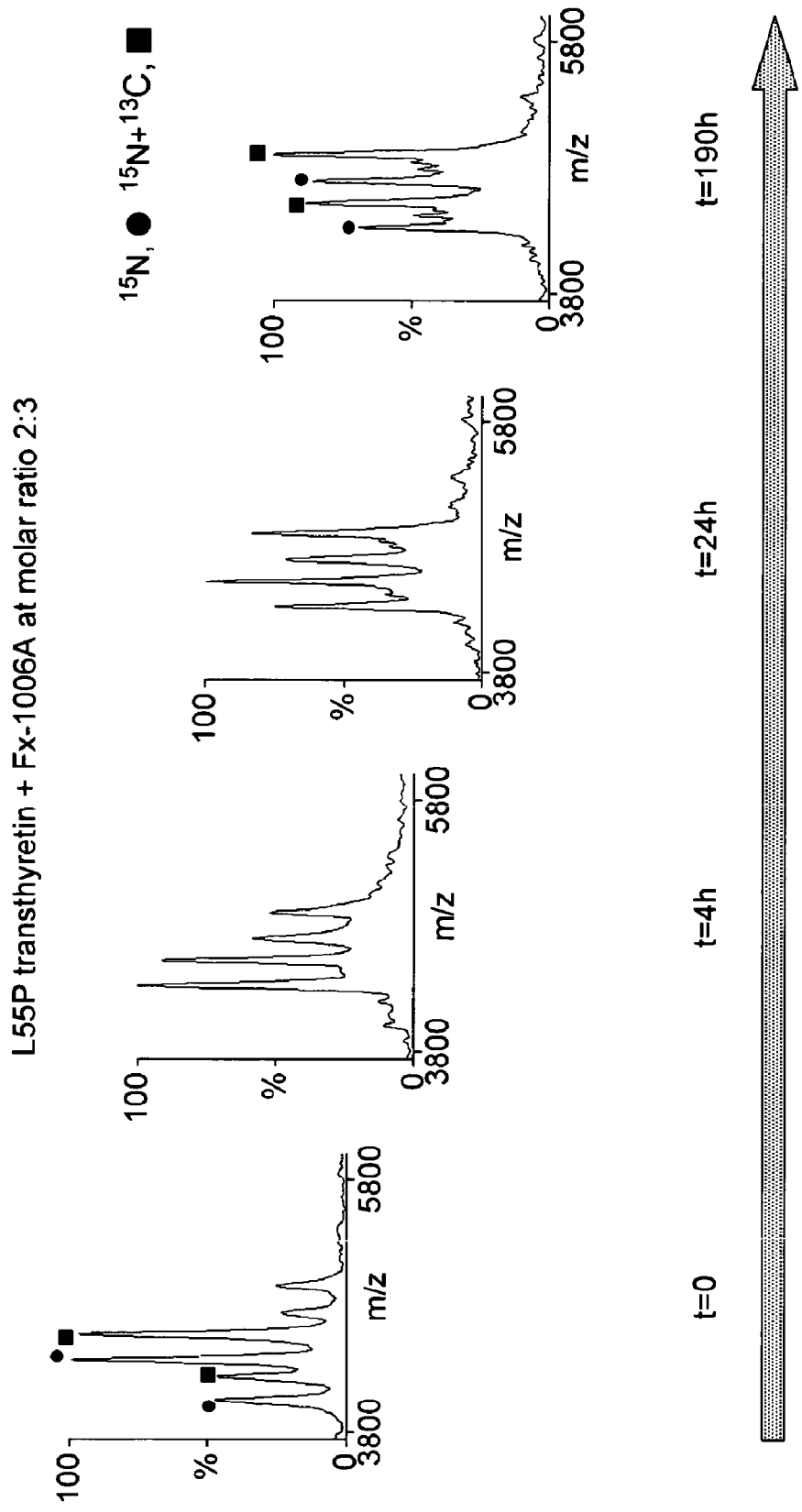
Figure 14:
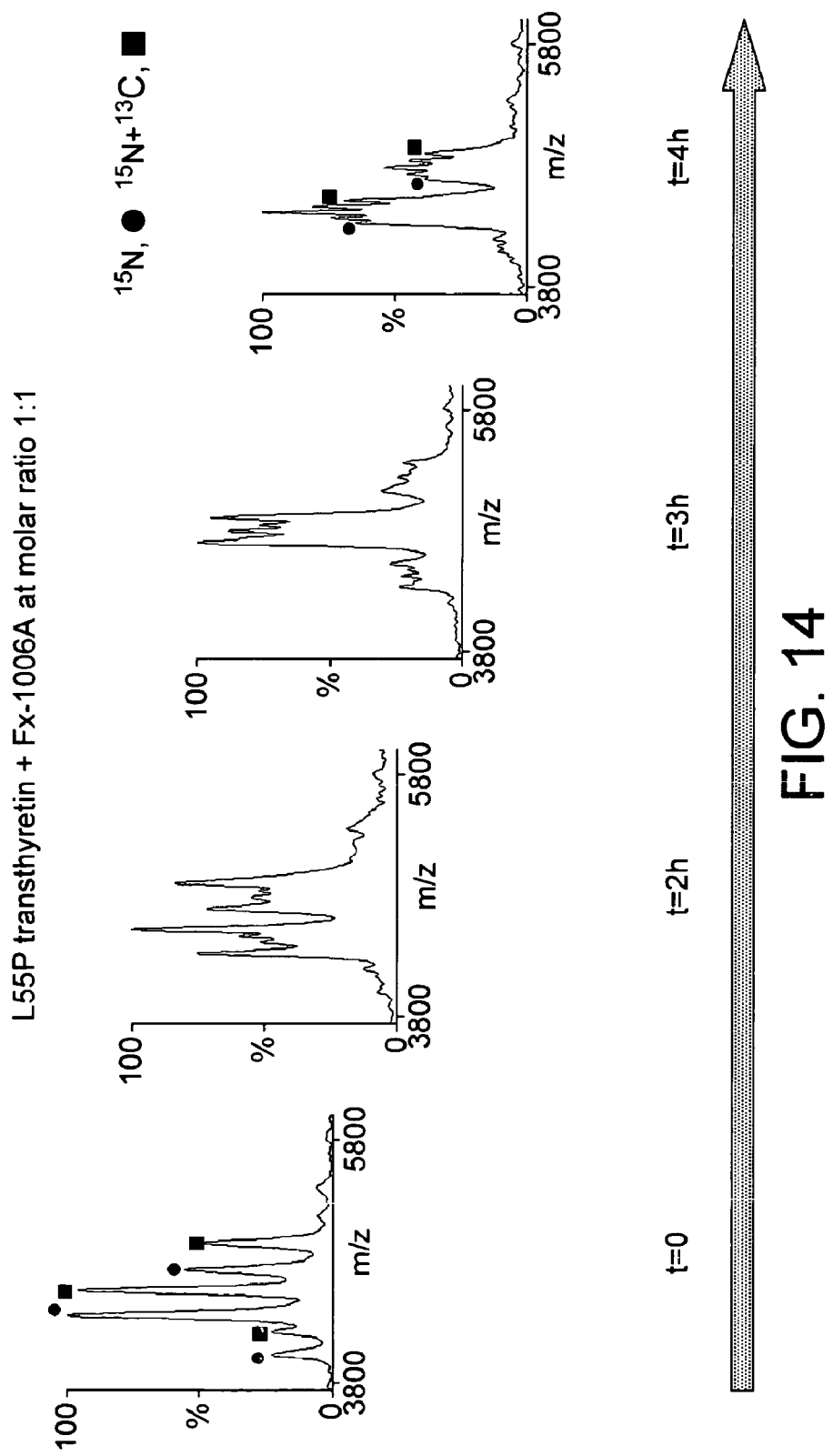
Figure 15:
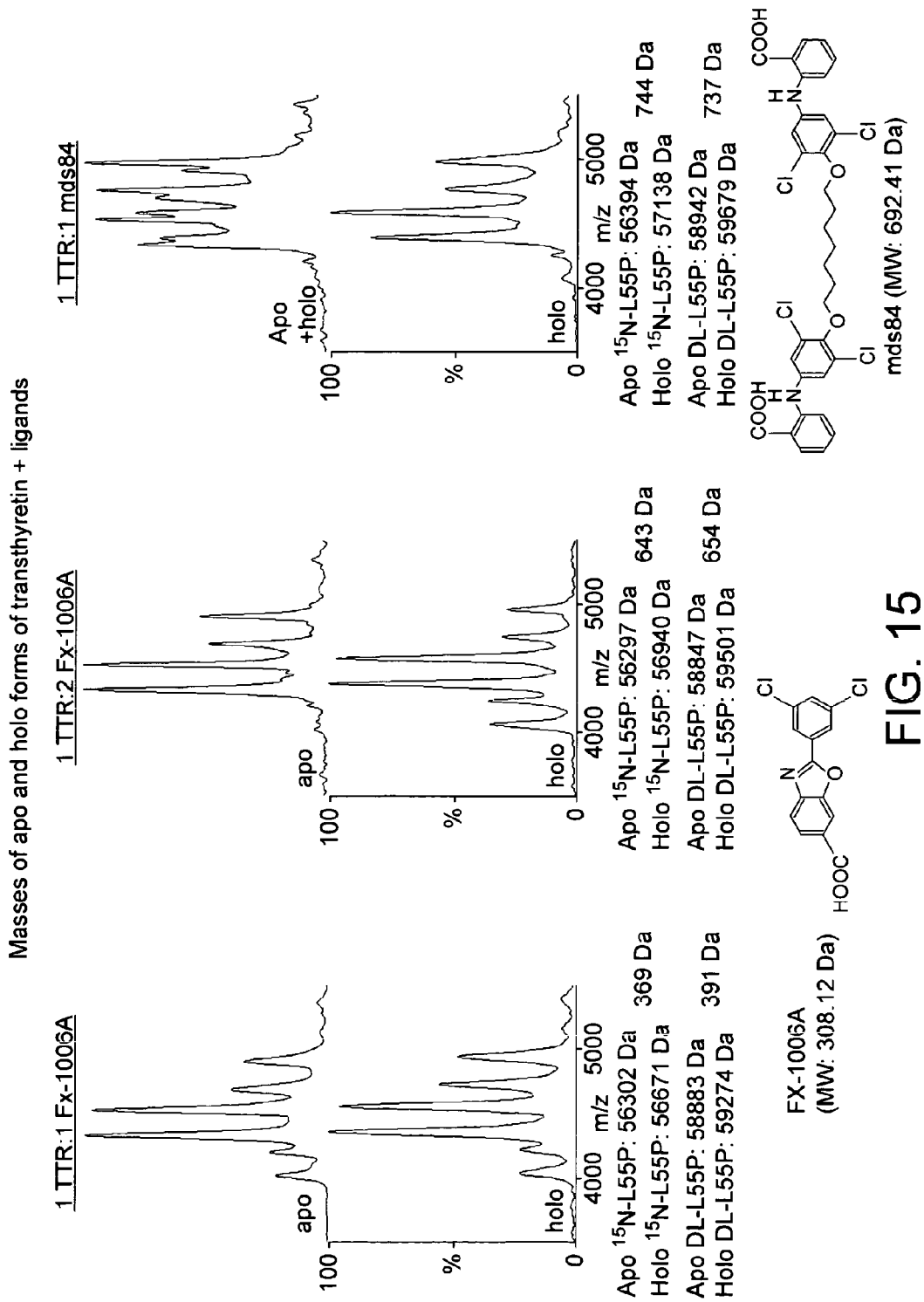
FIG. 15 shows mass spectra of transthyretin alone and with ligands mds84 and Fx-1006A.

In further experiments the capacity of mds84 and of Fx-1006A were compared with respect to inhibition of subunit exchange in L55P variant transthyretin. This most unstable transthyretin variant rapidly undergoes spontaneous and extensive subunit exchange, as illustrated in FIG. 8. FIGS. 9-11 show the effects of decreasing molar ratios of mds84 on inhibition of subunit exchange. FIGS. 12-14 show the effects of decreasing molar rations of Fx-1006A in the same analysis. FIG. 15 demonstrates that at the molar ratios shown there is complete uptake of the respective ligands into complexes with tetrameric transthyretin molecules. It is clear that one mole of mds84 is bound per mole of transthyretin and that this binding completely inhibits all subunit exchange. At lower molar ratios of mds84 some exchange takes place but the transthyretin molecules which bind mds84 are still completely stabilized. In contrast complete stabilization by Fx-1006A requires binding of two moles of ligand per mole of transthyretin, and at lower molar ratios stabilization is notably less effective.

4.3. Mass spectrometric analysis of dissociation of 4ajm15 from wild type and amyloidogenic variant transthyretin. ESMS spectra were acquired under increasing cone voltage conditions to induce stepwise dissociation of the ligand from wild type transthyretin and amyloidogenic variants V30M and L55P transthyretin. As the cone voltage increases splitting becomes apparent in the tetramer peaks, corresponding to apo (protein alone) and holo (protein+ligand) transthyretin as ligand begins to dissociate. The onset of ligand dissociation and/or the height of apo transthyretin peak demonstrate that the relative binding avidities for 4ajm15 are wild type transthyretin<V30M transthyretin<L55P transthyretin. Indeed dissociation of 4ajm15 from L55P transthyretin can be observed only at higher collisional energy than wild type (FIG. 8).

Figure 16:
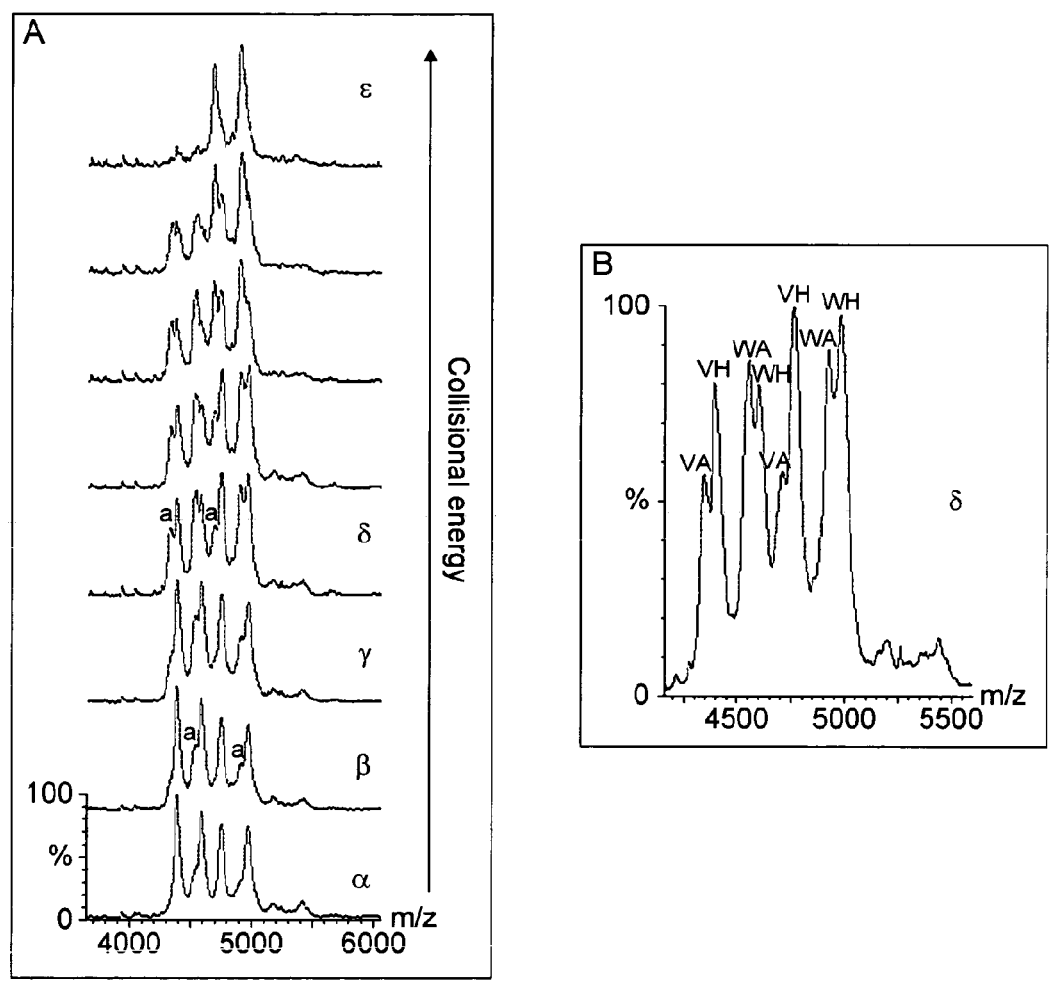
FIG. 16 shows mass spectra of transthyretin tetramer during ligand dissociation.

FIG. 16 shows mass spectra acquired for an equimolar solution (4.4 µM) of [$^{15}$N] L55P transthyretin and [$^{15}$N, $^{13}$C] wild type transthyretin in a 2 fold excess of 4ajm15. FIG. 16A shows transthyretin tetramer spectra during ligand dissociation. In spectrum β the onset of 4ajm15 dissociation from wild type tetramer is observed (a) while no ligand dissociation is observed from L55P transthyretin. Dissociation from wild type transthyretin progresses with increasing collisional energy in spectrum γ, but it is not until spectrum δ, where approximately 50% of the wild type is apo, that ligand dissociation from L55P transthyretin is observed (a). FIG. 16B shows a close up of the tetramer portion of spectrum δ, VA=apo L55P, VH=holo L55P, WA=apo wild type, WH=holo wild type).

Figure 17:
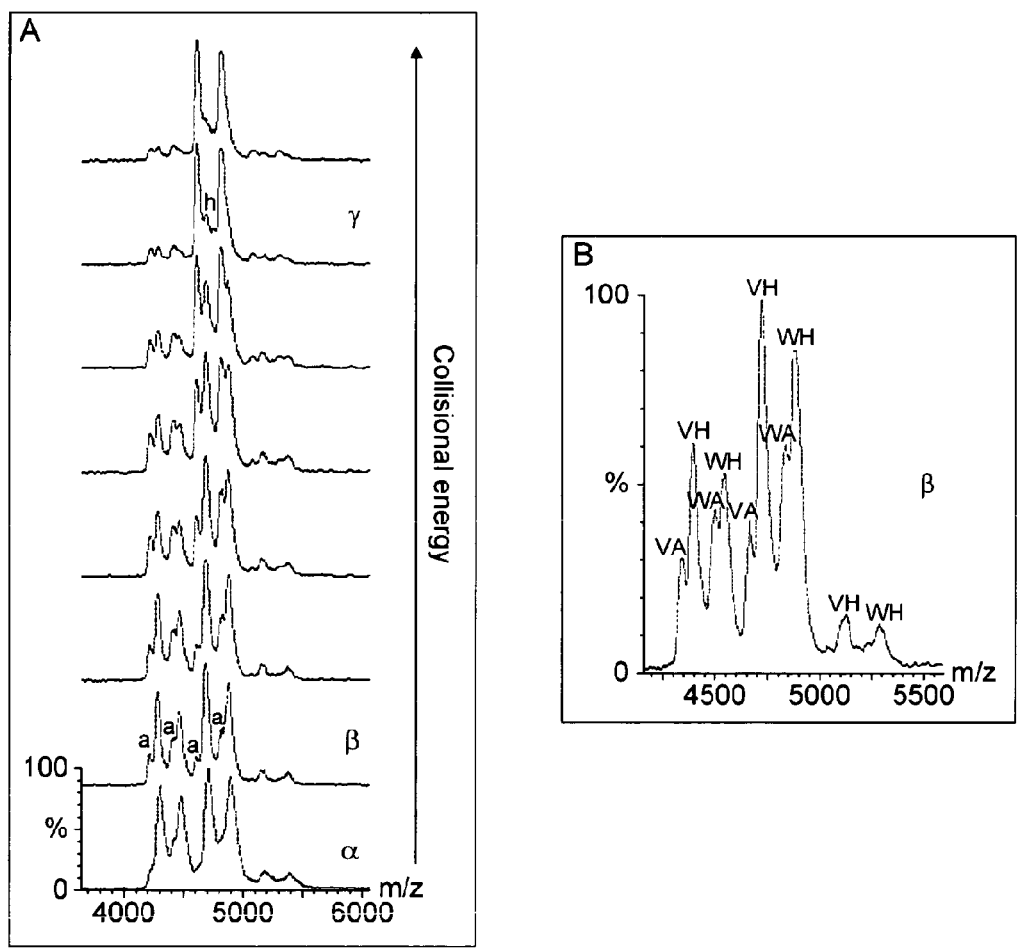
FIG. 17 shows mass spectra of ligand dissociation from V30M transthyretin.

The onset of ligand dissociation from V30M transthyretin occurs at the same energy level but the peak height corresponding to apo V30M transthyretin is lower than that for wild type (FIG. 17). Since these two species have very similar amino acid sequences (and therefore similar charging during MS ionisation) they are able to act as internal standards for each other. Therefore a lower peak height for apo V30M compared to apo WT is indicative of a lower proportion of apo V30M than apo WT. At increasing energy levels apo V30M is consistently lower relative to apo WT and as ligand dissociation from WT is complete, a proportion of holo V30M is still present. These results clearly show that 4ajm15 is more strongly bound by the less stable amyloidogenic variant transthyretin tetramers than by the wild type.

FIG. 17 shows mass spectra acquired for an equimolar solution (4.4 µM) of [$^{15}$N] V30M transthyretin and [$^{15}$N, $^{13}$C] wild type transthyretin in a 2 fold excess of ligand. In A, at the onset of 4ajm15 dissociation (spectrum β) the peak height corresponding to apo V30M transthyretin is lower than that for wild type (labelled a and a respectively) for each charge state. At high energy level (γ), ligand dissociation from wild type is complete while a proportion of hobo V30M remains (h). In B, a close up of the tetramer portion of spectrum β shows that peak heights for apo V30M average ~45%, while that from wild type is closer to 75%. VA, apo variant (V30M), VH, hobo variant (V30M), WA, apo wild type, WH, holo wild type.

5. X-Ray Crystallography Studies

Following the pioneering work of Blake and co-workers (1978) on the 3D structure determination of transthyretin, the Protein Data Bank now contains a large number of related structures. These include structures of amyloidosis associated variant proteins and a range of ligand complexes, determined using laboratory based X-ray sources and synchrotron radiation. Cody and co-workers (Neumann et al 2005) have determined a number of structures with bound thyroxine, the natural ligand for transthyretin, and analogues, and highlighted the problems associated with the interpretation of electron density maps and the refinement of these complexes when the ligand is positioned on a crystal symmetry axis. Some of the other protein-ligand complexes that have been deposited in the data bank have not been determined at high resolution and map interpretation may have placed too much reliance on other structures. We have carried out a number of high resolution structure analyses of transthyretin-ligand complexes, sometimes revisiting earlier work, that have provided critical insights beyond those available in the literature as to the nature of the ligand binding site and how it might be targeted with drugs of high binding affinity.

5.1 3,5,3',5'-Tetraiodo-L-Thyronine (L-Thyroxine, T4)

Crystals of transthyretin with bound L-thyroxine (T4) were grown at room temperature over the course of two weeks using the hanging drop method. Each drop contained 2 µl of 24 mg/ml transthyretin, 1 µl of 30 mM T4 in 50% dimethylsulphoxide (DMSO), and 3 µl well solution composed of 50 mM sodium acetate buffer pH 4.0, 100 mM NaCl and 25% polyethyleneglycol 550 monomethyl ether (PEG 550 MME). Data were collected at 100K on beam line ID14.2 at the European Synchrotron Radiation Source (ESRF), and processed using Mosflm (Leslie, 1992), programs from the CCP4 suite (CCP4, 1994), and SHELX (Sheldrick and Schneider, 1997). Statistics from the structure determination are shown in Table 3 below.

Figure 18:
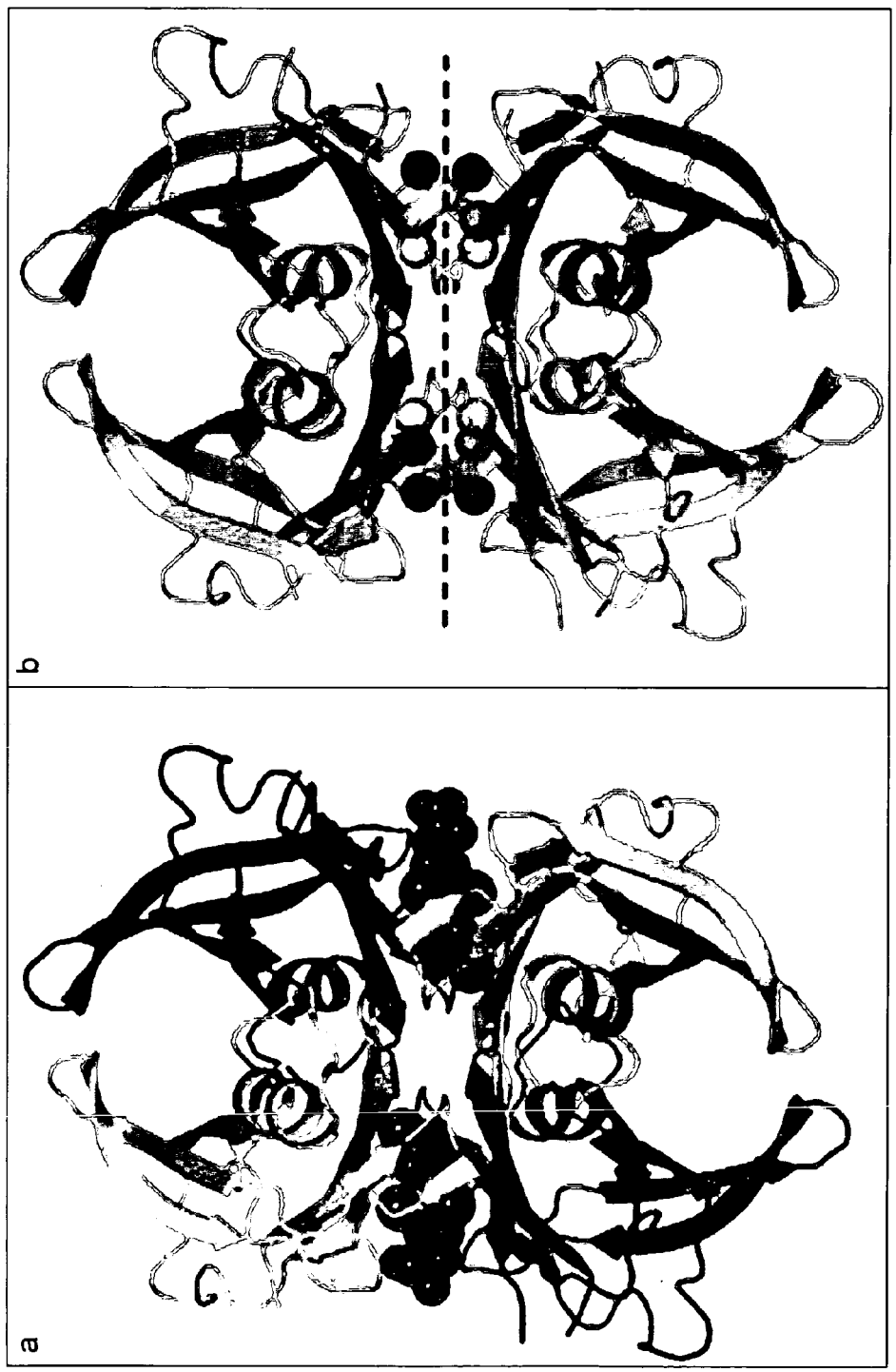
FIG. 18 shows L-thyroxine bound to transthyretin tetramer.

T4 is the major form of thyroid hormone found in the blood but only 10-15% of this is carried by transthyretin (Hamilton et al. 2001). There are currently seven structures of T4 bound to various forms of transthyretin in the international protein databank, with the structure 1ETB (1.7 Å resolution) representing the highest resolution structure for T4 and native human transthyretin deposited to date (Hamilton et al, 1993), although more recent high resolution structures have been reported for native transthyretin alone and drug complexes, including a dibromobenzoxazole complex showing reverse mode binding (Johnson et al, 2008). We have solved a transthyretin-T4 complex structure with cell dimensions (43 Å×86 Å×65 Å, 90°×90°×90°, $P2_12_12$) to a significantly higher resolution of 1.2 Å. This structure has enabled detailed analysis and definition of the three halogen binding pockets on each transthyretin subunit, with the high resolution data allowing a more precise definition of the multiple conformations available to the T4 molecule. FIG. 18 shows a) transthyretin tetramer showing the four monomers and the location of the two L-thyroxine molecules; and. b) transthyretin tetramer showing the location of three pairs of halogen binding pockets—inner, middle and outer, and crystallographic 2-fold (dashed line).

The ligand binding site in this space group (common to the majority of transthyretin structures solved to date) lies across the two-fold symmetry axis. As a consequence two orientations of T4 can be built into the density. In both orientations the T4 is bound in the "forward" orientation with the iodines pointing towards the centre of the protein, resolving an ambiguity seen in some other lower resolution structures (Muziol et al, 2001). Furthermore, the high quality of the maps has allowed us to establish accurately the three distinct positions available to pairs of halogen atoms within the transthyretin binding site, providing crucial guidance in the development and optimisation of new ligands. These observations go beyond the scope of the currently published literature (Johnson et al, 2005).

5.2 4ajm15

Crystals of transthyretin with bound 4ajm15 were grown at room temperature over the course of two weeks using the hanging drop method. Each drop contained 1 µl of 10 mg/ml transthyretin, of a slurry containing approximately 10 mM 4ajm15 in 10 mM sodium acetate pH 6.0 buffer with 60% DMSO, and 2 µl well solution composed of 70 mM sodium acetate buffer pH 4.0, 100 mM NaCl and 25% PEG 550 MME. Data were collected at 100K on beam line ID14.2 at the ESRF, and processed using Mosflm (Leslie, 1992), programs from the CCP4 suite (CCP4, 1994), and SHELX (Sheldrick and Schneider, 1997). Statistics from the structure determination are shown in Table 3 below.

Figure 19:
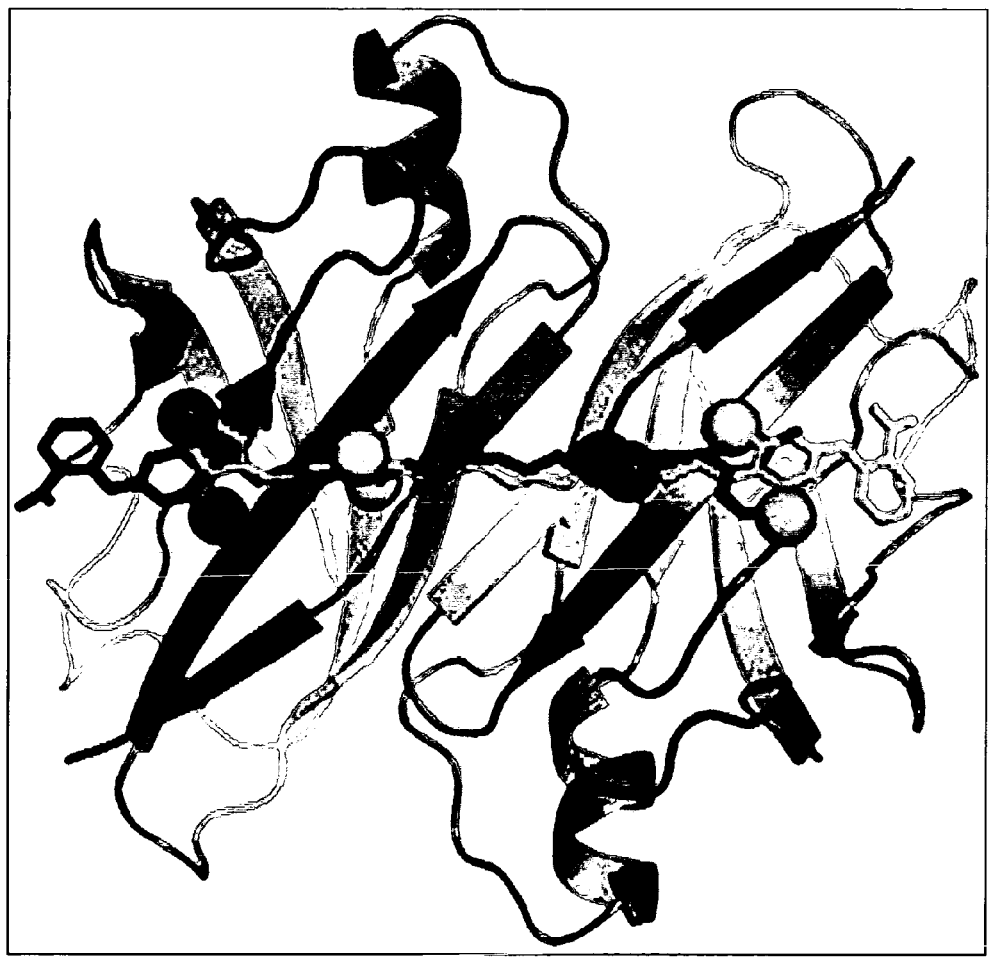
FIG. 19 shows 4ajm15 bound through the middle of transthyretin tetramer.

The bivalent ligand 4ajm15 was constructed from a bis-arylamine compound with chlorine substituents on the three and the five position, cross linked via an oxygen on each head group and an 11 carbon linker. The head group of this compound had previously been reported to be bound tightly by the transthyretin tetramer, with its chloride substituted rings pointing towards the outside of the protein (Oza et al, 2002). The selection of this orientation may well have derived from observations of T4 binding where the outer halogens occupy unique positions and the inner halogens are distributed between two positions. Transthyretin was co-crystallised with the 4ajm15 compound and data collected. The crystals were in the same space group as the complex of transthyretin with T4. However, the electron density for the ligand was found to be ambiguous. Based on our studies of the transthyretin-T4 complex structure we were able to determine that 4ajm15 was bound in four orientations—two due to the symmetry axis as before, but a further two based on the shuttling of the compound between the inner and outer halogen pockets. Contrary to expectations it seemed that 4ajm15 bound through the middle of the transthyretin tetramer with each head group bound in the opposite orientation to that previously reported in the literature. FIG. 19 shows two orientations of 4ajm15 demonstrating the sliding effect between the inner and outer halogen pockets. Chlorines are shown as large spheres. As the distance between the two ligand binding sites of each transthyretin molecule was only 9.5 Å, and the central 11 carbon chain of the linker was approximately 11.5 Å, each 4ajm15 molecule could be bound with only one head group occupying the inner halogen binding pocket, while the second was forced into the outer halogen binding pocket. Based on this observation, and coupled with biophysical data suggesting that 4ajm15 is bound with high affinity by transthyretin, we designed a new ligand, designated mds84, with the same head groups but a shortened cross-linker containing only 7 carbon atoms.

5.3 mds84

Crystals of transthyretin bound to mds84 were grown at room temperature over the course of two weeks using the hanging drop method. Each drop was made up of a 3 µl slurry containing approximately 15 mg/ml transthyretin and 25 mM mds84 in 10 mM sodium acetate pH 6.0 buffer with 60% DMSO, and 3 µl well solution composed of 70 mM sodium acetate buffer pH 4.5, 100 mM NaCl and 25% PEG 550 MME. Data were collected at 100K on beamline ID14.1 at the ESRF, and processed using Mosflm (Leslie, 1992), programs from the CCP4 suite (CCP4, 1994), and SHELX (Sheldrick and Schneider, 1997). Statistics from the structure determination are shown in Table 3 below.

Figure 20:
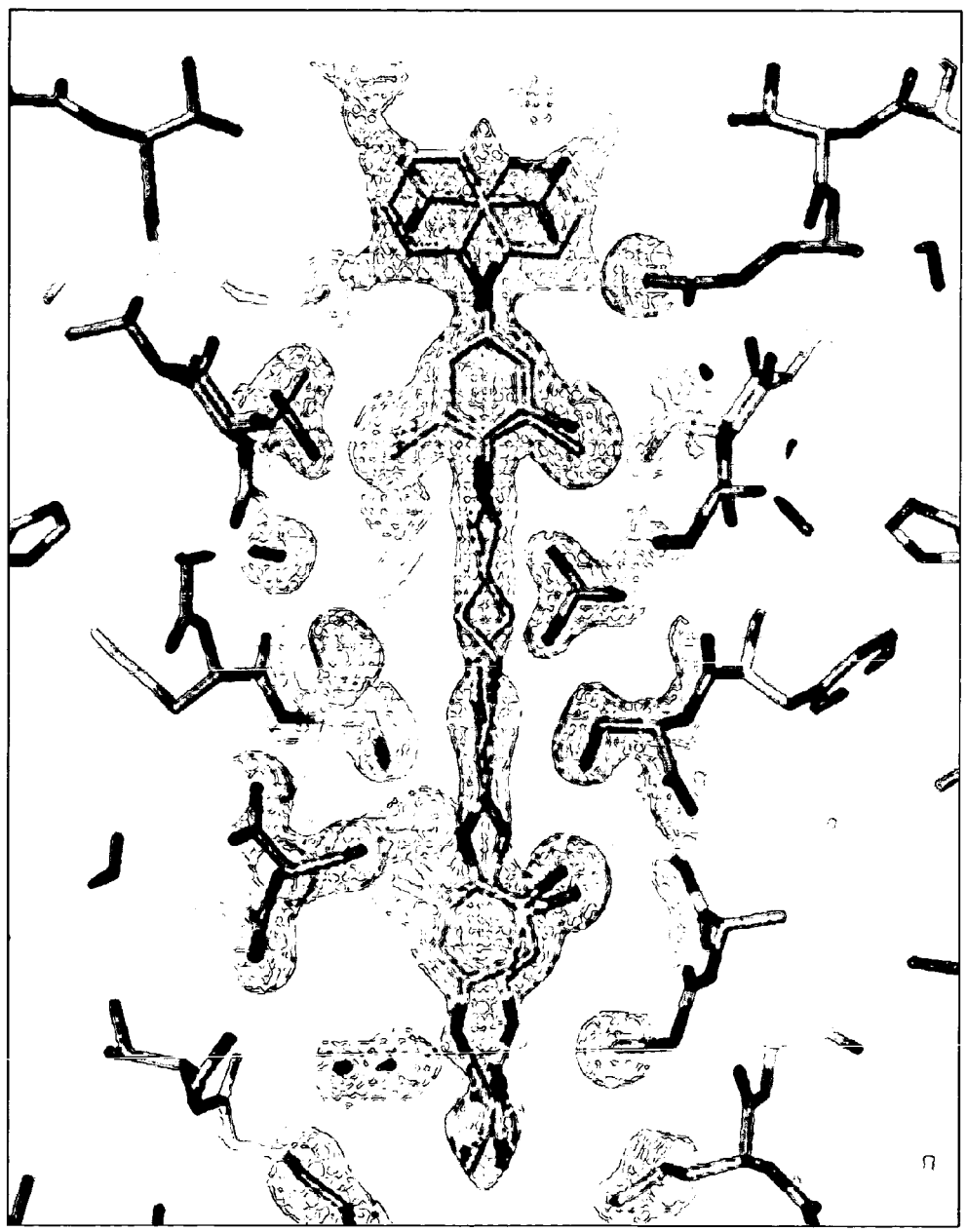
FIG. 20 shows mds84 bound through the middle of the transthyretin tetramer.

Data collected to 1.4 Å resolution at the ESRF in Grenoble for crystals of transthyretin complexed with the shorter, 7 carbon, linked palindromic bis-aryl compound mds84 confirmed its binding through the middle of the transthyretin tetramer. With the shorter linker chain length each head group was able to occupy the inner higher affinity halogen binding pocket. FIG. 20 shows 2Fo-Fc density contoured at 1.0× sigma showing two symmetry related mds84 molecules. Good density is seen for the chloride substituted rings in the inner halide binding pockets and for the seven carbon linker. Biophysical measurements show that this compound is avidly bound by the transthyretin tetramer.

Figure 21:
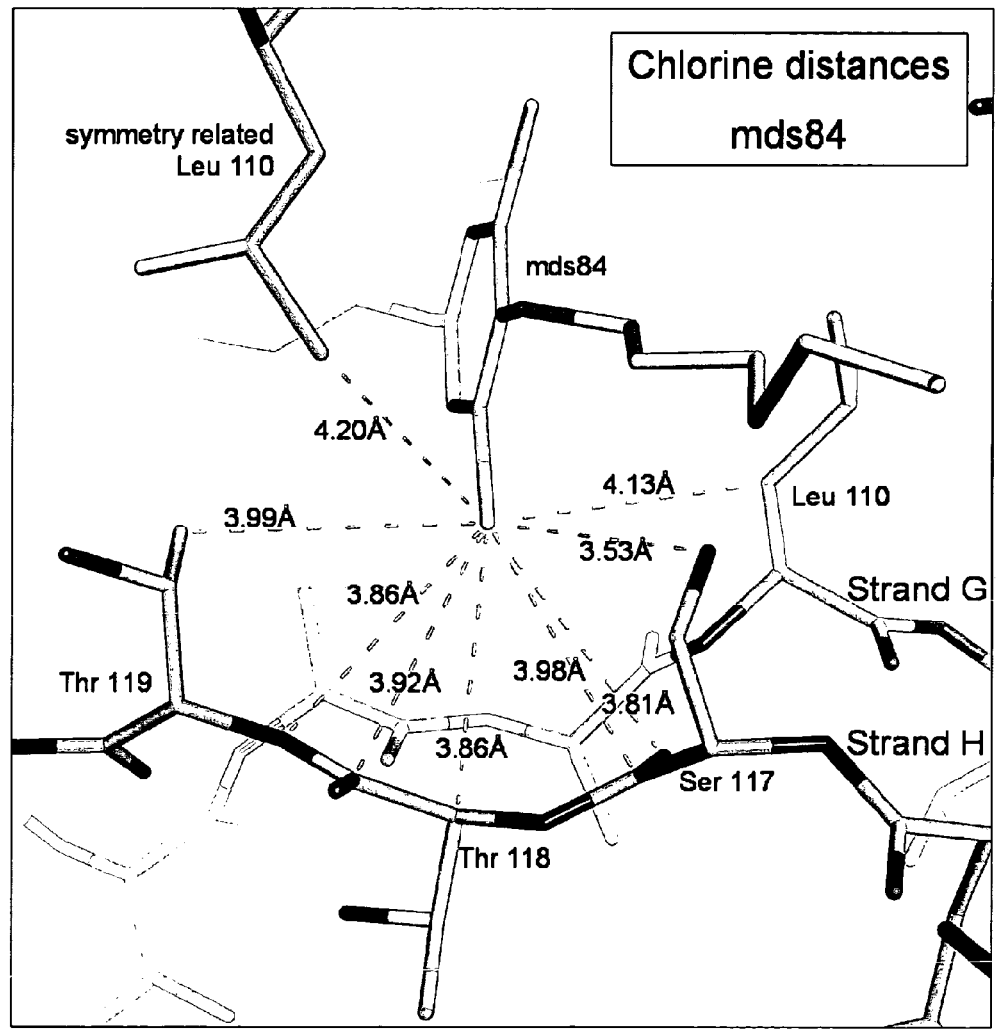
FIG. 21 shows details of the transthyretin inner binding cavity with bound mds84.

The chlorine substituents of 4ajm15 and mds84 project towards strands G and H of the transthyretin protomer (reference protomer) and the binding pocket is defined by neighbouring peptide main chain and side-chain atoms. The closest contacts are made with strand H. This strand forms an antiparallel β-sheet with strand H' of a local symmetry axis related protomer to make up the asymmetric unit of the crystal. Van der Waals interactions of less than 4 Å are made with predominantly main chain atoms of Ser117, Thr118 and Thr119. The enclosure of the chlorines is completed by a range of more distant atoms. The side-chain of Leu110 from strands G of adjacent crystal symmetry related subunits sandwich the chlorine substituted aromatic ring but atoms Cβ and Cδ2" are positioned within 4.2 Å of the chlorine atom of the reference protomer. The linker atom and the anthranilic acid ring are enclosed by the side-chains of Leu17 (strand A), Lys15 (strand A), Val121 (strand H), Ala108 (strand G) and their crystal symmetry mates. The acidic group approaches the terminal side-chain amino group of both Lys15 residues. The neighbours defining the chlorine pocket in the complex of transthyretin with bound mds84 are illustrated in FIG. 21.

TABLE 3

Structure determination statistics for crystals of transthyretin bound to test compounds

|  | T4 | 4ajm15 | mds84 |
| --- | --- | --- | --- |
| Space Group | $P2_12_12$ | $P2_12_12$ | $P2_12_12$ |
| Unit-cell parameters | a = 43.083 | a = 42.999 | a = 43.241 |
|  | b = 85.736 | b = 85.706 | b = 84.876 |
|  | c = 63.982 | c = 63.791 | c = 63.390 |
| Resolution Range in Å | 51.3-1.2 | 51.30-1.3 | 35-1.4 |
| Multiplicity (Outer Shell) | 7.0 (5.0) | 7.5 (6.8) | 7.4 (5.1) |
| Completeness (Outer Shell) | 94.1 (67.8) | 97.8 (94.3) | 98.3 (90.3) |
| $R_{meas}$ (Outer Shell) | 0.066 (0.741) | 0.075 (0.30) | 0.062 (0.85) |
| I/SigI (Outer Shell) | 15.7 (2.0) | 17.8 (6.4) | 16.5 (2.0) |
| Unique Reflections (Outer Shell) | 91,224 (9379) | 57,561 (7974) | 45,900 (6035) |
| R factor | 21.3 | 21.9 | 17.5 |
| $R_{free}$ | 25.9 | 24.5 | 20.7 |

Structural Formulae of Selected Compounds

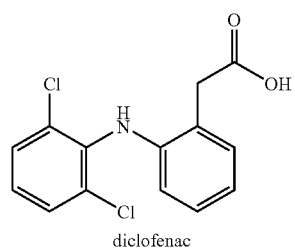

diclofenac (1)

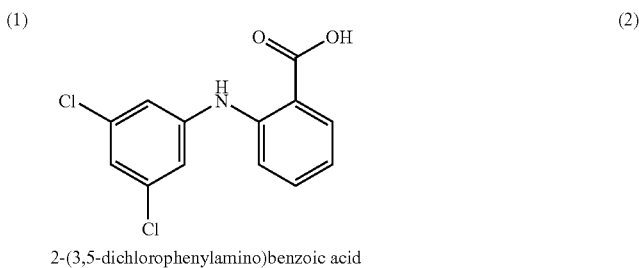

2-(3,5-dichlorophenylamino)benzoic acid (2)

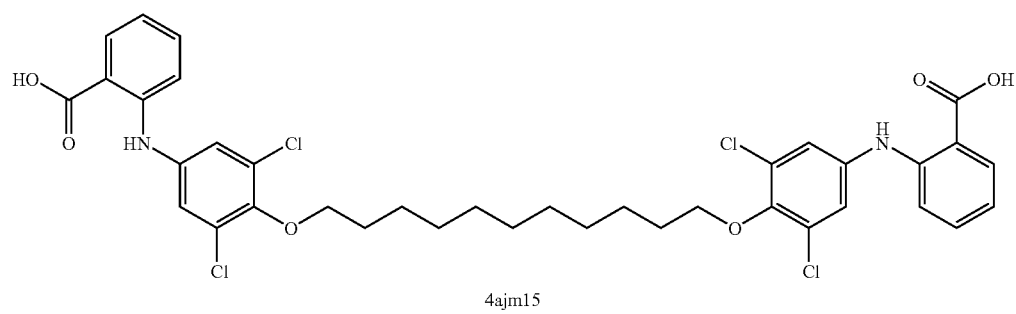

4ajm15 (3)

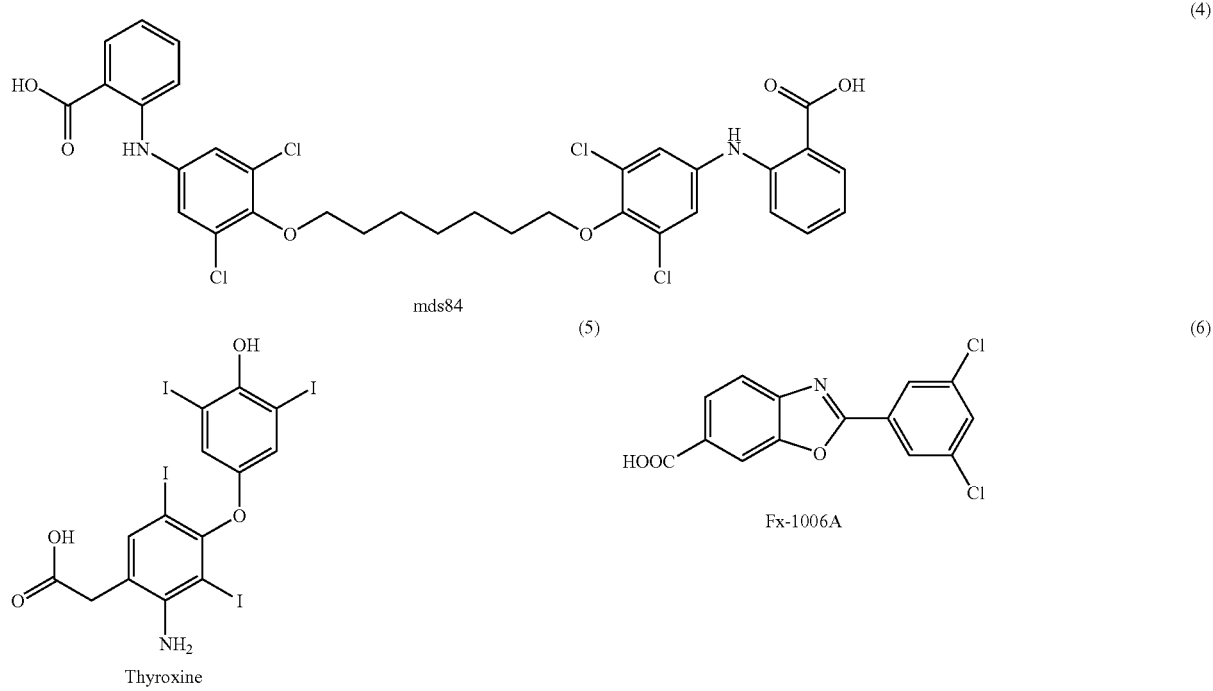

References

Almeida, M. R., Damas, A. M., Lans, M. C., Brouwer, A., Saraiva, M. J. Thyroxine binding to transthyretin Met 119. Comparative studies of different heterozygotic carriers and structural analysis. Endocrine 1997; 6: 309-315.

Blake, C. C., Geisow, M. J., Oatley, S. J., Rerat, B., Rerat, C. Structure of prealbumin: secondary, tertiary and quaternary interactions determined by Fourier refinement at 1.8 A. J. Mol. Biol. 1978; 121: 339-356.

Collaborative Computational Project, Number 4. The CCP4 Suite: Programs for Protein Crystallography. Acta Cryst. 1994; D50: 760-763.

Colon, W., Kelly, J. W. Partial denaturation of transthyretin is sufficient for amyloid fibril formation in vitro. Biochemistry 1992; 31: 8654-8660.

Green, N. S., Palaninathan, S. K., Sacchettini, J. C., Kelly, J. W. Synthesis and characterization of potent bivalent amyloidosis inhibitors that bind prior to transthyretin tetramerization. JACS 2003; 125: 13404-13414.

Hamilton, J. A., Benson, M. D. Tranthyretin: a review from a structural perspective. Cell. Mol. Life. Sci. 2001; 58: 1491-1521.

Hamilton, J. A., Steinrauf, L. K., Braden, B. C., Liepnieks, J., Benson, M. D., Holmgren, G., Sandgren, O., Steen, L. The X-ray crystal structure refinements of normal human Transthyretin and the amyloidogenic Val-30 Met variant to 1.7 Å resolution. J. Biol. Chem. 1993; 268: 2416-2424.

Jacobson, D. R., Pastore, R. D., Yaghoubian, R., Kane, I., Gallo, G., Buck, F. S., Buxbaum, J. N. Variant-sequence transthyretin (isoleucine 122) in late-onset cardiac amyloidosis in black Americans. N. Engl. J. Med., 1997; 336: 466-473.

Jeppsson, J. O., Laurel, C. B., Franzen, B. Agarose gel electrophoresis. Clin. Chem. 1979; 25: 629-638.

Johnson, S. M., Wiseman, R. L., Sekijima, Y., Green, N. S., Adamski-Werner, S. L., Kelly, J. W. Native state kinetic stabilization as a strategy to ameliorate protein misfolding diseases: a focus on the transthyretin amyloidoses. Acc. Chem. Res. 2005; 38: 911-921.

Johnson S M, Connelly S, Wilson I A, and Kelly J W. (2008) Biochemical and Structural Evaluation of Highly Selective 2-Arylbenzoxazole-Based Transthyretin Amyloidogenesis Inhibitors J. Med. Chem. 51, 260-270

Keetch, C. A., Bromley, E. H. C., McCammon, M., Wang, N., Christodoulou, J., Robinson, C. V. J. Biol. Chem. 2005; 280: 41667-41674.

Laue, T. M., Shah, B. D., Ridgeway, T. M., Pelletier, S. L. Computer-aided interpretation of analytical sedimentation data for proteins. In: Analytical Sedimentation in Biochemistry and Polymer Science (Harding, S. E., Rowe, A. J., Horton, J. C., Eds.). The Royal Society of Chemistry, Cambridge, UK. 1992; pp. 90-125.

Leslie, A. G. W. Recent changes to the MOSFLM package for processing film and image plate data. Joint CCP4+ESF-EAMCB Newsletter on Protein Crystallography, No. 26, 1992.

Malpeli, G., Folli, C., Berni, R. Retinoid binding to retinol-binding protein and the interference with the interaction with transthyretin. *Biochim. Biophys. Acta* 1996; 1294: 48-54.

Miller, S. R., Sekijima, Y., Kelly, J. W. Native state stabilization by NSAIDs inhibits transthyretin amyloidogenesis from the most common familial disease variants. Lab. Invest. 2004; 84: 545-552.

Miroy, G. J., Zhihong, L., Lashuel, H. A., Peterson, S. A., Strang, C., Kelly, J. Inhibiting transthyretin amyloid fibril formation via protein stabilization. Proc. Natl. Acad. Sci. USA 1996; 93: 15051-15056.

Muziol, T., Cody, V., Luft, J. R., Pangborn, W., Wojtczak, A. Complex of rat transthyretin with tetraiodothyroacetic acid refined at 2.1 and 1.8 A resolution. Acta Biochim. Pol. 2001; 48: 877-884.

Nettleton, E. J., Sunde, M., Lai, Z., Kelly, J. W., Dobson, C. M., Robinson, C. V. Protein subunit interactions and structural integrity of amyloidogenic transthyretins: evidence from electrospray mass spectrometry. J. Mol. Biol. 1998; 281: 553-564.

Neumann, P., Cody, V., Wojtczak, A. Ligand binding at the transthyretin tetramer interface: crystal structure of transthyretin-T4AC complex at 2.2 A resolution. Acta Crystallogr. Sect. D 2005; 61: 1313-1319.

Oza, V. B., Smith, C., Raman, P., Koepf, E. K., Lashuel, H. A., Petrassi, H. M., Chiang, K. P., Powers, E. T., Sachettinni, J., Kelly, J. W. Synthesis, structure, and activity of diclofenac analogues as transthyretin amyloid fibril formation inhibitors. J. Med. Chem. 2002; 45, 321-323.

Pepys, M. B. Amyloidosis. Annu. Rev. Med. 2006; 57: 223-241.

Perkins, S. J. Protein volumes and hydration effects: the calculation of partial specific volumes, neutron scattering matchpoints and 280 nm absorption for proteins and glycoproteins from aminoacid sequences. Eur. J. Biochem. 1986; 157: 169-180.

Petrassi, H. M., Klabunde, T., Pacchettini, J., Kelly, J. W. Structure-based design of N-phenyl phenoxazine Transthyretin amyloid fibril inhibitors. J. Am. Chem. Soc. 2000; 122: 2178-2192.

Razavi, Hossein; Palaninathan, Satheesh K.; Powers, Evan T.; Wiseman, R. Luke; Purkey, Hans E.; Mohamedmohaideen, Nilofar N.; Deechongkit, Songpon; Chiang, Kyle P.; Dendle, Maria T. A.; Sacchettini, James C.; Kelly, Jeffery W. Benzoxazoles as transthyretin amyloid fibril inhibitors: Synthesis, evaluation, and mechanism of action. Angewandte Chemie, International Edition 2003; 42: 2758-2761.

Hossein Razavi, Evan T. Powers, Hans E. Purkey, Sara L. Adamski-Werner, Kyle P. Chiang, Maria T. A. Dendle and Jeffery W. Kelly Design, synthesis, and evaluation of oxazole transthyretin amyloidogenesis inhibitors. Bioorganic & Medicinal Chemistry Letters 2005; 15:1075-1078. Supplementary information at http://www.sciencedirect.com/science/MiamiMultiMediaURL/B6TF9-4F7SOXG-2/B6TF9-4F7SOXG-2-2/5221/ d55e766d188439424df55a77168d53c2/Data.doc Reay, P. Use of N-bromosuccinimide for the iodination of proteins for radioimmunoassay. Ann. Clin. Biochem. 1982; 19: 129-133.

Robbins, J. Transthyretin from discovery to now. Clin. Chem. Lab. Med. 2002; 40:1183-1190.

Saraiva, M. J. M., Costa, P. P., Goodman, D. S. Transthyretin (prealbumin) in familial amyloidotic polyneuropathy: genetic and functional aspects. Adv. Neurol. 1988; 48: 189-200.

Saraiva, M. J. Hereditary transthyretin amyloidosis: molecular basis and therapeutical strategies. Expert Rev. Mol. Med. 2002; 2002: 1-11.

Scheider, F., Hammarstrom, P., Kelly, J. W. Transthyretin slowly exchanges subunits under physiological conditions: a convenient chromatographic method to study subunit exchange in oligomeric proteins. Protein Sci. 2001; 10: 1606-1613.

Schuck, P. SEDFIT and SEDPHAT. 2005. http://www.analyticalultracentrifugation.com Schuck, P. Size distribution analysis of macromolecules by sedimentation velocity ultracentrifugation and Lamm equation modelling. Biophys. J. 2000; 78: 1606-1619.

Sheldrick, G., Schneider, T. SHELXL: high-resolution refinement. Methods Enzymol. 1997; 277: 319-343.

Sobott, F., Hernandez, H., McCammon, M. G., Tito, M. A., Robinson, C. V. A tandem mass spectrometer for improved transmission and analysis of large macromolecular assemblies. Anal. Chem. 2002; 74:1402-1407.

Sunde, M., Serpell, L. C., Bartlam, M., Fraser, P. E., Pepys, M. B., Blake, C. C.F. Common core structure of amyloid fibrils by synchrotron X-ray diffraction. J. Mol. Biol. 1997; 273: 729-739.

Terazaki, H., Ando, Y., Suhr, O., Ohlsson, P. L., Obayashi, K., Yamashita, T., Yoshimatsu, S., Suga, M., Uchino, M., Ando, M. Post-translational modification of transthyretin in plasma. Biochem. Biophys. Res. Commun. 1998; 249: 26-301.

White, J. T., Kelly, J. W. Support for the multigenic hypothesis of amyloidosis: the binding stoichiometry of retinol-binding protein, vitamin A, and thyroid hormone influences transthyretin amyloidogenicity in vitro. Proc. Natl. Acad. Sci. USA 2001; 98: 13019-13024.

Wiseman, R. L., Johnson, S. M., Kelker, M. S., Foss, T., Wilson, I. A., Kelly, J. W. Kinetic stabilization of an oligomeric protein by a single ligand binding event. JACS 2005; 127:5540-5551.

The invention will now be further described by the following paragraphs:

1. Agent for stabilising the tetrameric form of transthyretin, which comprises a compound of the general formula (I) or a pharmaceutically acceptable salt, ester or prodrug thereof:

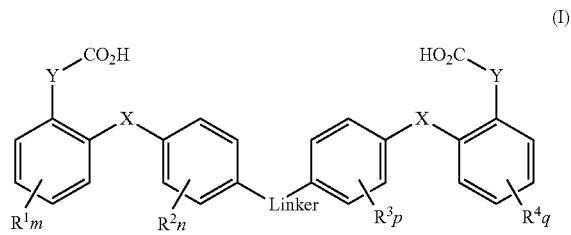

wherein:

each Y is independently a direct bond or —$CH_2$—;

each X is independently —NH—, —O—, —S—, —$CH_2$—, —NR—, —CO—, —CONH—, —CONR—, —C=N—O—, NHCO—, —NRCO—, —O—N=C—, —SO—, —$SO_2$— or a direct bond, wherein each of $R^1$, $R^2$, $R^3$ and $R^4$ is independently F, Cl, Br, I, $CF_3$, $OCF_3$, R', OR', NR'R', SOR' or $SO_2R'$, wherein R and R' are each independently $C_1$-$C_3$alkyl which is straight or branched chain or cyclic optionally substituted by one or more halogen atoms;

and each m, n, p and q is independently 0 to 4, wherein m+n+p+q>0;

and wherein the linker is a linear or branched chain of 7 to 13 carbon atoms in which one or more of the carbon atoms are optionally replaced by a heteroatom, wherein the said chain is unsubstituted or substituted by one or more groups comprising halogen, O, or N atoms, or OH, $C_1$-$C_3$ alkyl, $C_2$-$C_3$ alkenyl, $C_2$-$C_3$ alkynyl or $C_1$-$C_3$ alkoxy.

2. Agent according to paragraph 1, wherein m=q=0.

3. Agent according to paragraph 1 or paragraph 2, wherein n=p>0.

4. Agent according to paragraph 3, wherein n=p=2.

5. Agent according to paragraph 4, wherein the rings bearing $R^2$ and $R^3$ are each meta-disubstituted relative to X.

6. Agent according to any preceding paragraph, wherein $R^2$ and $R^3$ are each independently I, Br, Cl, F.

7. Agent according to paragraph 6, wherein R² and R³ are each Cl.

8. Agent according to any preceding paragraph, wherein X is NH.

9. Agent according to any preceding paragraph, wherein Y is a direct bond.

10. Agent according to paragraph 1, wherein the linker is —O—(CH₂)ᵣ—O— in which r is an integer of from 5 to 11.

11. Agent according to any preceding paragraph, which comprises a homobivalent compound.

12. Agent according to paragraph 1, having the following formula:

(II)

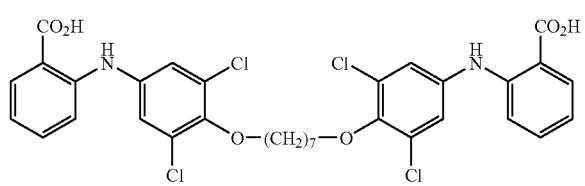

or a pharmaceutically acceptable salt or ester thereof.

13. Agent according to paragraph 1, having the following formula:

(III)

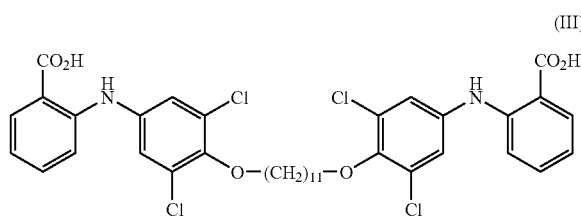

or a pharmaceutically acceptable salt or ester thereof.

14. Agent according to any preceding paragraph, for use in the treatment or prevention of transthyretin amyloidosis.

15. Agent according to paragraph 14, wherein the transthyretin amyloidosis comprises systemic transthyretin amyloidosis.

16. Use of an agent according to any one of paragraphs 1 to 13, for the manufacture of a medicament for treatment or prevention of transthyretin amyloidosis.

17. Use according to paragraph 16, wherein the transthyretin amyloidosis comprises systemic transthyretin amyloidosis.

18. A pharmaceutical composition comprising an agent according to paragraph 1 in admixture with one or more pharmaceutically acceptable excipients, diluents or carriers.

19. A method for stabilising the tetrameric form of transthyretin in a patient in need thereof, comprising administering to the patient a therapeutic amount of an agent according to claim 1 or a pharmaceutical composition according to paragraph 18.

What is claimed is:

1. A compound of the general formula (I) or a pharmaceutically acceptable salt, ester or prodrug thereof:

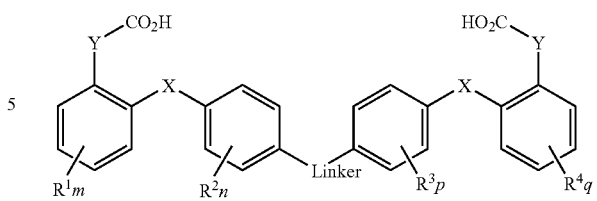

wherein:
each Y is independently a direct bond or —CH₂—;
each X is independently —NH—, —O—, —S—, —CH₂—, —NR—, —CO—, —CONH—, —CONR—, —C=N—O—, —NHCO—, —NRCO—, —O—N=C—, —SO—, —SO₂— or a direct bond, wherein
each of R¹, R², R³ and R⁴ is independently F, Cl, Br, I, CF₃, OCF₃, R', OR', NR'R', SOR' or SO₂R',
wherein R and R' are each independently C₁-C₃ alkyl which is straight or branched chain or cyclic optionally substituted by one or more halogen atoms;
and each m, n, p and q is independently 0 to 4, wherein m+n+p+q>0;
and wherein the linker is —O—(CH₂)ᵣ—O— in which r is an integer of from 5 to 11.

2. A compound according to claim 1, wherein m=q=0.

3. A compound according to claim 1 wherein n=p>0.

4. A compound according to claim 1, wherein n=p=2.

5. A compound according to claim 1, wherein the rings bearing R² and R³ are each meta-disubstituted relative to X.

6. A compound according to claim 5, wherein R² and R³ are each independently I, Br, Cl, F.

7. A compound according to claim 6, wherein R² and R³ are each Cl.

8. A according to claim 1, wherein X is NH.

9. A compound according to claim 1, wherein Y is a direct bond.

10. A compound according to claim 1, which comprises a homobivalent compound.

11. A compound according to claim 1, having the following formula:

(II)

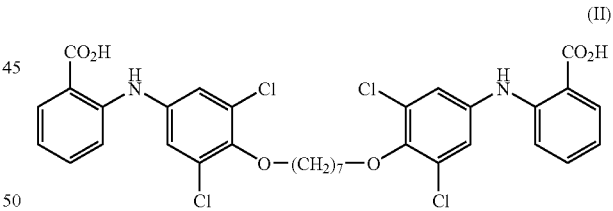

or a pharmaceutically acceptable salt or ester thereof.

12. A compound according to claim 1, having the following formula:

(III)

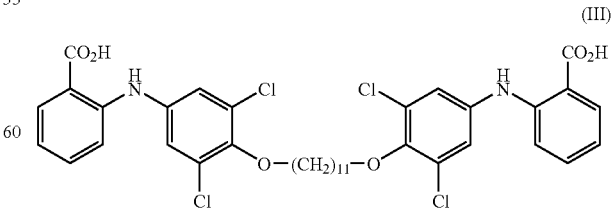

or a pharmaceutically acceptable salt or ester thereof.

13. A compound according to claim 1, for use in the treatment or prevention of transthyretin amyloidosis.

14. A compound according to claim 13, wherein the transthyretin amyloidosis comprises systemic transthyretin amyloidosis.

15. A method for the manufacture of a medicament for treatment or prevention of transthyretin amyloidosis comprising preparing a compound of claim 1.

16. Method according to claim 15, wherein the transthyretin amyloidosis comprises systemic transthyretin amyloidosis.

17. A pharmaceutical composition comprising a compound according to claim 1 in admixture with one or more pharmaceutically acceptable excipients, diluents or carriers.

18. A method for stabilizing the tetrameric form of transthyretin in a patient in need thereof, comprising administering to the patient a therapeutic amount of a compound according to claim 1 or a pharmaceutical composition according to claim 17.

* * * * *